United States Patent
Xie et al.

(10) Patent No.: US 8,027,032 B2
(45) Date of Patent: Sep. 27, 2011

(54) MICROSCOPY IMAGING SYSTEM AND METHOD EMPLOYING STIMULATED RAMAN SPECTROSCOPY AS A CONTRAST MECHANISM

(75) Inventors: Xiaoliang Sunney Xie, Lexington, MA (US); Christian Freudiger, Boston, MA (US); Wei Min, Cambridge, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 387 days.

(21) Appl. No.: 12/196,746

(22) Filed: Aug. 22, 2008

(65) Prior Publication Data
US 2010/0046039 A1 Feb. 25, 2010

(51) Int. Cl.
*G01J 3/44* (2006.01)
(52) U.S. Cl. ...................................... 356/301
(58) Field of Classification Search ............... 356/301
See application file for complete search history.

(56) References Cited

U.S. PATENT DOCUMENTS

| | | | | |
|---|---|---|---|---|
| 5,243,983 | A * | 9/1993 | Tarr et al. | 356/301 |
| 6,151,522 | A * | 11/2000 | Alfano et al. | 356/301 |
| 6,798,507 | B2 | 9/2004 | Xie et al. | |
| 6,809,814 | B2 | 10/2004 | Xie et al. | |
| 7,352,458 | B2 | 4/2008 | Xie et al. | |
| 7,388,668 | B2 | 6/2008 | Potma et al. | |
| 7,414,729 | B2 | 8/2008 | Xie et al. | |
| 2003/0007145 | A1* | 1/2003 | Shimada | 356/301 |
| 2008/0037595 | A1 | 2/2008 | Gankkhanov et al. | |
| 2009/0073432 | A1* | 3/2009 | Jalali et al. | 356/301 |

OTHER PUBLICATIONS

Levine et al. "Frequency-modulated shot noise limited stimulated Raman gain spectroscopy", Feb. 15, 1980, Applied Physics Letters, vol. 36, pp. 245-247.*
Levenson et al., "FM spectroscopy detection of stimulated Raman gain" Optics Letters, vol. 8, No. 2, Feb. 1983, pp. 108-110.
EPO Search Report issued on May 3, 2010 in connection with corresponding EPO Application No. 09010121.3.
Ganikhanov et al.,"High-sensitivity vibrational imaging with frequency modulation coherent anti-Stokes Raman scattering (FM CARS) microscopy", Optics Letters, vol. 31, No. 12, Jun. 15, 2006, pp. 1872-1874.

(Continued)

*Primary Examiner* — Kara E Geisel
(74) *Attorney, Agent, or Firm* — Gesmer Updegrove LLP

(57) ABSTRACT

A microscopy imaging system includes a first light source for providing a first train of pulses at a first center optical frequency $\omega_1$, a second light source for providing a second train of pulses at a second center optical frequency $\omega_2$, a modulator system, an optical detector, and a processor. The modulator system is for modulating a beam property of the second train of pulses at a modulation frequency f of at least 100 kHz. The optical detector is for detecting an integrated intensity of substantially all optical frequency components of the first train of pulses from the common focal volume by blocking the second train of pulses being modulated. The processor is for detecting, a modulation at the modulation frequency f, of the integrated intensity of the optical frequency components of the first train of pulses to provide a pixel of an image for the microscopy imaging system.

43 Claims, 16 Drawing Sheets

OTHER PUBLICATIONS

Saikan et al., "Inverse Raman Spectroscopy in Dye Solutions with Synchronized CW Picosecond Lasers", Optics Communications, vol. 51, No. 6, Oct. 15, 1984, pp. 420-424.

Volkmer, "Vibrational imaging and microspectroscopies based on coherent anti-Stokes Raman scattering (CARS)" XP 002561572, FRISNO-8, Feb. 25, 2005.

Proceedings of the IRE, Nov. 1962, printed from IEEE Xplore on Nov. 3, 2008, pp. 2365-2383.

N. Bloembergen, "The Stimulated Raman Effect," American Journal of Physics, Nov. 1967, pp. 989-1023.

A. Owyoung, "Sensitivity Limitations for CW Stimulated Raman Spectroscopy," Optics Communication, vol. 22, No. 3, Sep. 1977, pp. 323-328.

A. Owyoung, "Coherent Raman Gain Spectroscopy Using CW Laser Sources," IEEE Journal of Quantum Electronics, vol. QE-14, No. 3, Mar. 1978, pp. 192-203.

B. Levine et al., "Surface Vibrational Spectroscopy Using Stimulated Raman Scattering," IEEE Journal of Quantum Electronics, vol. QE-15, No. 12, Dec. 1979, pp. 1418-1432.

B. Levine et al., "Ultrahigh Sensitivity Stimulated Raman Gain Spectroscopy," IEEE Journal of Quantum Electronics, vol. QE-16, No. 1, Jan. 1980, pp. 85-89.

E. Ploetz et al., "Femtosecond stimulated Raman microscopy," Applied Physics B, 87, Mar. 2007, pp. 389-393.

* cited by examiner

MICROSCOPY IMAGING SYSTEM AND METHOD EMPLOYING STIMULATED RAMAN SPECTROSCOPY AS A CONTRAST MECHANISM

SPONSORSHIP INFORMATION

This invention was made with Government support under National Institutes of Health award 5DP1OD000277-05, Department of Energy award DE-FG02-07ER15875, and National Science Foundation award DBI-0649892. The Govermnent has certain rights in the invention.

BACKGROUND

The invention generally relates to vibrational microscopy and imaging systems, and relates in particular to vibrational imaging systems employing Raman scattering.

Conventional vibrational imaging techniques include, for example, infrared microscopy, Raman microscopy, and coherent anti-Stokes Raman scattering (CARS) microscopy.

Infrared microscopy, which generally involves directly measuring the absorption of vibrational excited states in a sample, is limited by poor spatial resolution due to the long wavelength of infrared light, as well as by a low penetration depth due to a strong infrared light absorption by the water in biological samples.

Raman microscopy records the spontaneous inelastic Raman scattering upon a single (ultraviolet, visible or near infrared) continuous wave (CW) laser excitation. Raman microscopy has improved optical resolution and penetration depth as compared to infrared microscopy, but the sensitivity of Raman microscopy is rather poor because of the very low spontaneous Raman scattering efficiency (Raman scattering cross section is typically on the order of $10^{-30}$ cm$^2$). This results in long averaging times per image, which limits the biomedical application of Raman microscopy.

CARS microscopy, which uses two pulsed laser beams (pump and Stokes beams), significantly increases the absolute scattering signal due to the coherent excitation. The CARS process, however, also excites a high level of background from the vibrationally non-resonant specimen. Such a non-resonant background not only distorts the CARS spectrum of the resonant signal from dilute sample but also carries the laser noise, significantly limiting the application of CARS microscopy on both spectroscopy and sensitivity perspectives.

One approach to reduce the non-resonant background field in CARS microscopy is to take advantage of the fact that the non-resonant background has different polarization properties than the resonant signal. For example, U.S. Pat. No. 6,798,507 discloses a system in which the pump and Stokes beams are properly polarized and a polarization sensitive detector is employed. Another approach to reducing the non-resonant background field involves detecting the anti-Stokes field in a reverse direction. U.S. Pat. No. 6,809,814 discloses a system in which a CARS signal is received in the reverse direction (epi-direction) from the sample. For transparent samples, however the epi directed signal is significantly smaller than the forward directed signal, and a stronger signal may be desired for certain applications.

There is a need, therefore, for a system and method for providing much improved sensitivity in vibrational imaging, and in particular, to provide a microscopy system that preserves the Raman spectrum (and the associated vibrational signature) and provides an output resonant signal that is readily distinguishable from the non-resonant background.

SUMMARY

The invention provides a microscopy imaging system in accordance with an embodiment of the invention that includes a first light source, a second light source, a modulator system, focusing optics, an optical detector, and a processor. The first light source is for providing a first train of pulses at a first center optical frequency $\omega_1$. The second light source is for providing a second train of pulses at a second center optical frequency $\omega_2$ such that a difference between $\omega_1$ and $\omega_2$ is resonant with a vibrational frequency of a sample in the focal volume. The second train of pulses is synchronized with the first train of pulses. The modulator system is for modulating a property of the second train of pulses at a modulation frequency f of at least 100 kHz. The focusing optics is for directing and focusing the first train of pulses and the second train of pulses toward a common focal volume. The optical detector is for detecting an integrated intensity of substantially all optical frequency components of the first train of pulses transmitted or reflected through the common focal volume while blocking the second train of pulses. The processor is for detecting, at the modulation frequency f, a modulation (amplitude and/or phase) of the integrated intensity of substantially all of the optical frequency components of the first train of pulses due to a non-linear interaction of the first train of pulses with the second train of pulses in the common focal volume, to provide a pixel of an image for the microscopy imaging system.

In accordance with another embodiment, the invention provides a microscopy imaging method that includes the steps of providing a first train of pulses at a first center optical frequency $\omega_1$; providing a second train of pulses at a second center optical frequency $\omega_2$ such that a difference between $\omega_1$ and $\omega_2$ is resonant with a vibrational frequency of a sample in the focal volume, wherein the second train of pulses is synchronized with the first train of pulses; modulating a property of the second train of pulses at a modulation frequency f of at least 100 kHz; directing and focusing the first train of pulses and the second train of pulses toward a common focal volume; detecting an integrated intensity of a plurality of optical frequency components of the first train of pulses transmitted or reflected through the common focal volume by blocking the second train of pulses; and detecting, at the modulation frequency f, a modulation (amplitude and/or phase) of the integrated intensity of the plurality of optical frequency components of the first train of pulses due to the non-linear interaction of the first train of pulses with the second train of pulses in the common focal volume, to provide a pixel of an image for the microscopy imaging system.

BRIEF DESCRIPTION OF THE ILLUSTRATED EMBODIMENTS

The following description may be further understood with reference to the accompanying drawings in which.

The drawings are shown for illustrative purposes only.

DETAILED DESCRIPTION

The invention provides, in accordance with an embodiment, a new vibrational imaging technique, herein referred to as stimulated Raman scattering microscopy, in which two pulsed laser beams (one pump beam and one Stokes beam) are jointly used to stimulate vibrational transitions, which leads to the intensity decrease (stimulated Raman loss) of the pump beam and intensity increase (stimulated Raman gain) of the Stokes beam. High-frequency modulation of a property of the pump beam or the Stokes beam is achieved, and a phase-sensitive detector is employed to measure the loss of the pump beam and/or gain of the Stokes beam due to the interaction of the beams.

Figure 1:
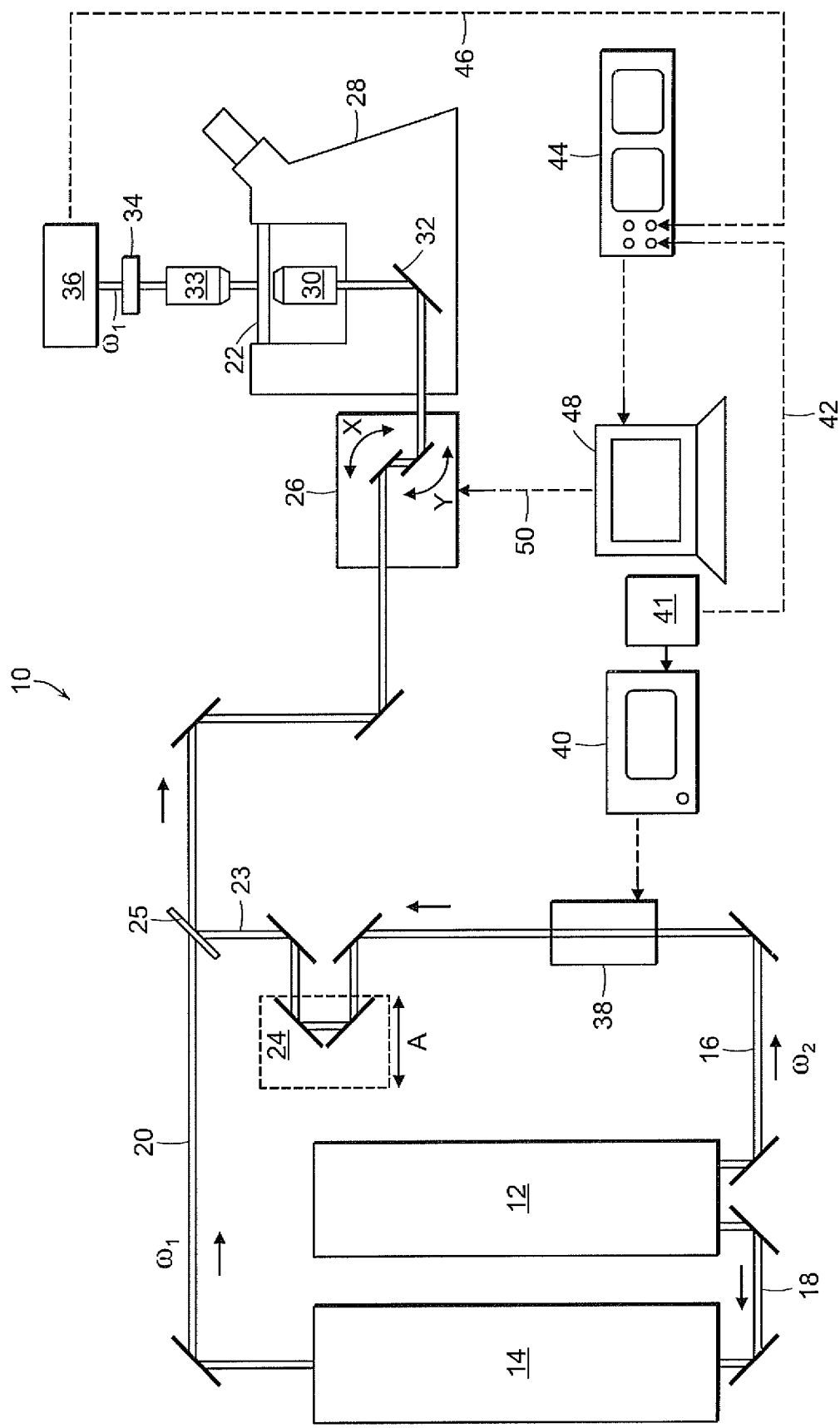
FIG. 1 shows an illustrative diagrammatic view of a microscopy imaging system in accordance with an embodiment of the invention.

FIG. 1, for example, shows a microscopy imaging system 10 in accordance with an embodiment of the invention that includes a dual frequency laser source 12 and an optical parametric oscillator 14. The dual frequency laser source 12 provides a train of laser pulses 16 at a center frequency $\omega_1$ (e.g., a Stokes frequency of about 1064 nm), and a train of laser pulses 18 at a different center frequency (e.g., 532 nm) to the optical parametric oscillator 14. The optical parametric oscillator may be, for example, as disclosed in U.S. Patent Application Publication No. 2008/0037595, the disclosure of which is hereby incorporated by reference in its entirety. The output of the optical parametric oscillator provides a train of laser pulses 20 at a center frequency $\omega_2$ (e.g., a pump frequency) that is selected such that a difference between $\omega_1$ and $\omega_2$ (e.g., $\omega_p - \omega_S$) is resonant with a vibrational frequency of a sample 22 in a focal volume. The train of laser pulses 16 at a center Stokes frequency is modulated by a modulation system, and is then adjusted at a translation stage 24 (that is adjustable as indicated at A) to ensure that the resulting train of laser pulses 23 and the train of laser pulses 20 at the center pump frequency are temporally overlapped. The two trains of laser pulses 23 and 20 are combined at a combiner 25 such that they are collinear and spatially overlapped as well.

The combined trains of laser pulses 16 and 20 are directed via a scanhead 26 (that scans in mutually orthogonal x and y directions), into a microscope 28 that includes optics 30 that direct and focus the combined trains of laser pulses 23 and 20 into the focal volume, e.g., via a mirror 32. The illumination from the focal volume is directed by a condenser 33 onto an optical detector 36, and the modulated beam $\omega_2$ (e.g., the Stokes beam) is blocked by an optical filter 34, such that the optical detector 36, such as a photodiode, measures the intensity of the other beam $\omega_1$ (e.g., the pump beam) only.

The train of laser pulses 23 is modulated at modulation frequency f, by a modulation system that includes, for example, a modulator 38, a controller 40, and a modulation source 41. The modulation source provides a common modulation control signal 42 to the controller 40 as well as to a signal processor 44. The integrated intensity of substantially all frequency components of the first pulse train 46 from the optical detector 36 is provided to the signal processor 44, and the modulation (amplitude and/or phase) of the integrated intensity of substantially all the optical frequency components of the train of laser pulses 20 due to the non-linear interaction of the train of laser pulses 23 with the train of laser pulses 20 in the focal volume is detected at the modulation frequency f to provide a pixel of an image to a microscopy control computer 48. The microscopy control computer 48 is employed as an imaging system, and further provides user control of the scanhead 26 as shown at 50.

Figure 2A:
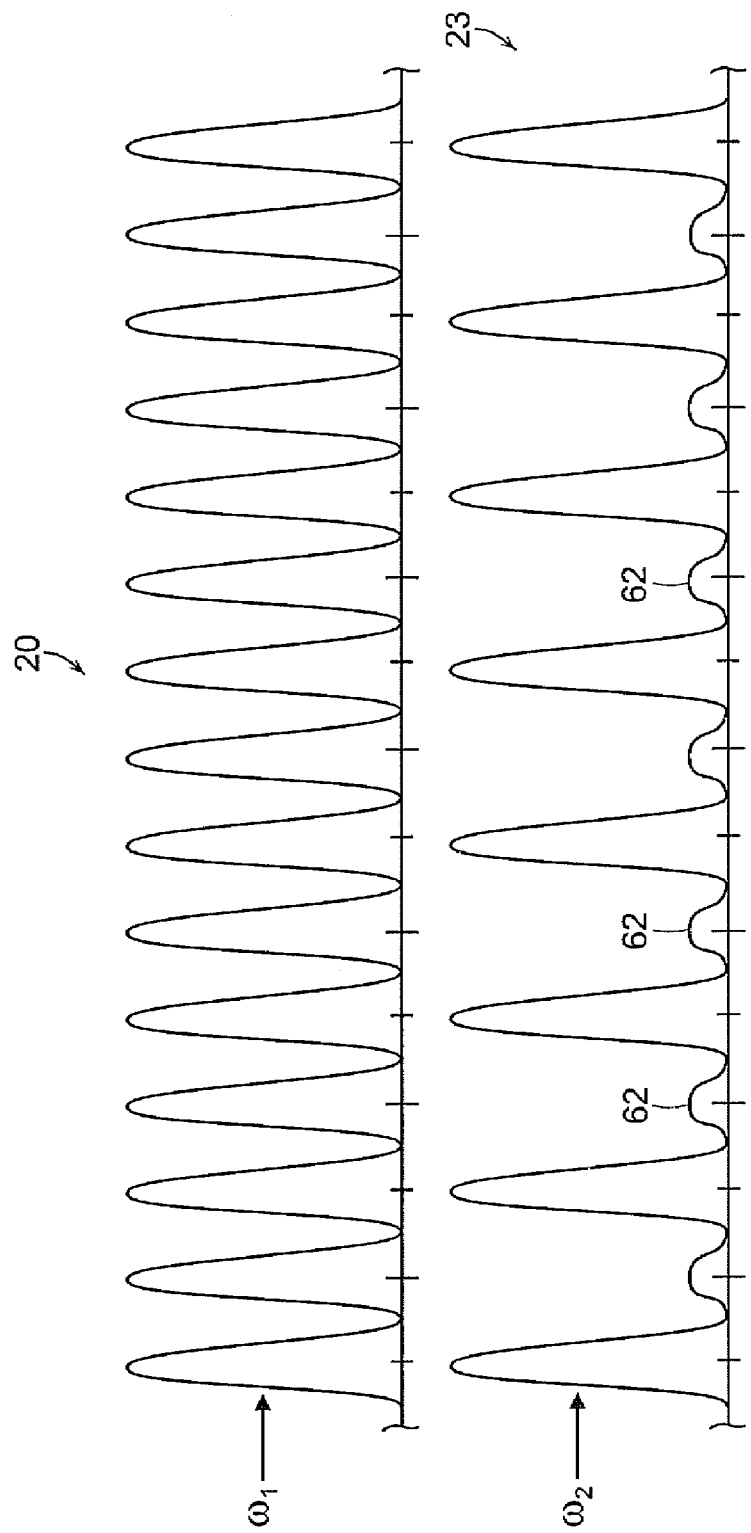
FIGS. 2A-2D show illustrative graphical representations of two pulse trains, one of which is modulated using amplitude modulation, polarization modulation, time-shifting modulation, and frequency modulation respectively in accordance with various embodiments of the invention.

In accordance with an embodiment, the modulation system may provide amplitude modulation of the $\omega_2$ beam to provide a modulated $\omega_2$ pulse train 23 such that only alternating pulses of the $\omega_2$ pulse train (16 shown in FIG. 1) are coincident with the pulses of the $\omega_1$ pulse train 20 as shown in FIG. 2A. Such amplitude modulation of the $\omega_2$ beam may be achieved using a Pockel cell and polarization analyzer as the modulator 38, and a Pockel cell driver as the controller 40. FIG. 2A shows an illustrative example in which the modulation rate is half the repetition rate of the laser such that every other pulse of the original $\omega_2$ pulse train is reduced in amplitude (as shown at 62) to provide that stimulated Raman scattering does not substantially occur in the focal volume with the pulses having the reduced amplitude. If the modulation rate is of the same order of the repetition rate of the laser, countdown electronics must be utilized to guarantee the synchronization (phase) between the modulation and the pulse train. A wide variety of different modulation rates are also possible. In further embodiments, the contrast pulses 62 may have an amplitude that is substantially zero by switching off the pulses at the modulation frequency, for example using an electro-optic modulator (such as a MEMs device or a galvanometric scanner) or an acousto-optic modulator.

Amplitude modulation of the pump or Stokes pulse trains may therefore be achieved, and the increase of the Stokes pulse train or decrease of the pump pulse train may be measured. This can be done with a Pockel Cell and a polarization analyzer.

By modulating the pump train of pulses and then detecting the Stokes train of pulses from the focal volume, Raman gain may be determined by the processing system. In further embodiments, the Stokes beam may be modulated, the pump beam may be detected from the focal volume, and Raman loss may be determined by the processing system.

The system of the above embodiment of the invention, therefore, provides that stimulated Raman scattering microscopy may be achieved using a modulation of one of the pump or Stokes beams as a contrast mechanism. Stimulated Raman scattering microscopy bears most of the advantages of the existing methods. In particular, (1) it is a optically stimulated process which significantly enhances the molecular vibrational transition efficiency compared to conventional Raman microscopy which relies on spontaneous scattering; (2) it is a nonlinear process in which the signal is only generated at the microscopy objective focus, rendering a three-dimensional sectioning ability; (3) it only probes the vibrational resonance, and it is free from interference with the non-resonant background, unlike in the CARS microscopy where non-resonant background is always present; (4) the signal always scales linearly with the solute concentration, allowing ready analytical quantification; (5) the signal can be free from sample auto-fluorescence; (6) the phase matching condition is always satisfied for any relative orientations of the beams, unlike in the CARS microscopy; (7) visible and near-IR beams are used resulting in a higher penetration depth and spatial resolution than IR absorption microscopy; and (8) the detection of Raman gain or loss is also unaffected by ambient light, which permits such systems to be used in open environments.

The process may be viewed as a two photon process for excitation of a vibrational transition. The joint action of one photon annihilated from the pump beam and one photon created to the Stokes beam promotes the creation of the molecular vibrational phonon. The energy of the pump photon is precisely converted to the sum of the energy of the Stokes photon and the molecular vibrational phonon. As in any two photon optical process, the transition rate is proportional to the product of the pump beam intensity and the Stokes beam intensity. It is obvious that a molecular vibrational level is necessary for this process to happen, as required by the energy conservation. There is, therefore, no contribution from non-resonant background would be present. This represents a significant advantage over CARS microscopy which is severely limited by non-resonant background which not only distorts the spectrum but also carries unwanted laser noise.

The process may also be treated as a stimulated version of the spontaneous Raman scattering. In spontaneous Raman scattering, the Stokes photon mode is empty in the initial state and the vacuum field serves as the stimulated Stokes beam. That is why the efficiency is extremely low. The transition rate is only proportional to the pump beam intensity. In stimulated Raman scattering however, the Stokes photon mode has a large number of pre-occupied photons due to the presence of a strong laser beam, and the scattering process becomes stimulated in analogy to the stimulated emission. As a result, the transition rate is proportional not only to the pump beam intensity as in spontaneous Raman scattering, but also to the number of pre-occupied photons in Stokes photon mode which is again proportional to the Stokes beam intensity.

The process may also be accounted for as a heterodyne interference between the pump beam (or the Stokes beam) and a corresponding third-order nonlinear induced radiation at the same optical frequency as the pump beam (or the Stokes beam). These two third-order nonlinear induced polarizations for stimulated Raman gain and loss are different from each other, and are also distinct from the one responsible for CARS generation. If there are no additional electronic resonances involved, however, their absolute sizes are all the same.

For stimulated Raman loss of the pump beam, this third-order nonlinear induced polarization radiates at the pump beam frequency. The intensity dependence of this nonlinear radiation scales linearly with pump beam and quadratically with Stokes beam. Its final phase is 180 degree lag behind that of the input pump beam at the far field detector. Therefore, the interference between this nonlinear radiation and input pump beam results in an attenuation of the pump beam itself. And the intensity dependence of the interference term scales linearly with both the pump beam and Stokes beam.

For stimulated Raman gain for Stokes beam, a different third-order nonlinear induced polarization radiates at the Stokes beam frequency. The intensity dependence of this nonlinear radiation scales quadratically with pump beam and linearly with Stokes beam. Its final phase is the same as that of the input Stokes beam at the far field detector. Therefore, the interference between this nonlinear radiation and input Stokes beam results in an increase of the Stokes beam itself. The intensity dependence of the interference term again scales linearly with both the pump beam and Stokes beam.

Two other closely related third-order nonlinear induced polarizations for non-resonant background are also excited by the input two laser beams, and radiating at pump frequency and the Stokes frequency, respectively. However, their relative phases are either 90 or 270 degree lag behind those of the pump beam or the Stokes beam at the far field detector. As a consequence of these orthogonal phase relationships, they do not interfere with the input pump beam or the Stokes beam, giving no detectable contribution to the loss or the gain of the signal.

Figure 2B:
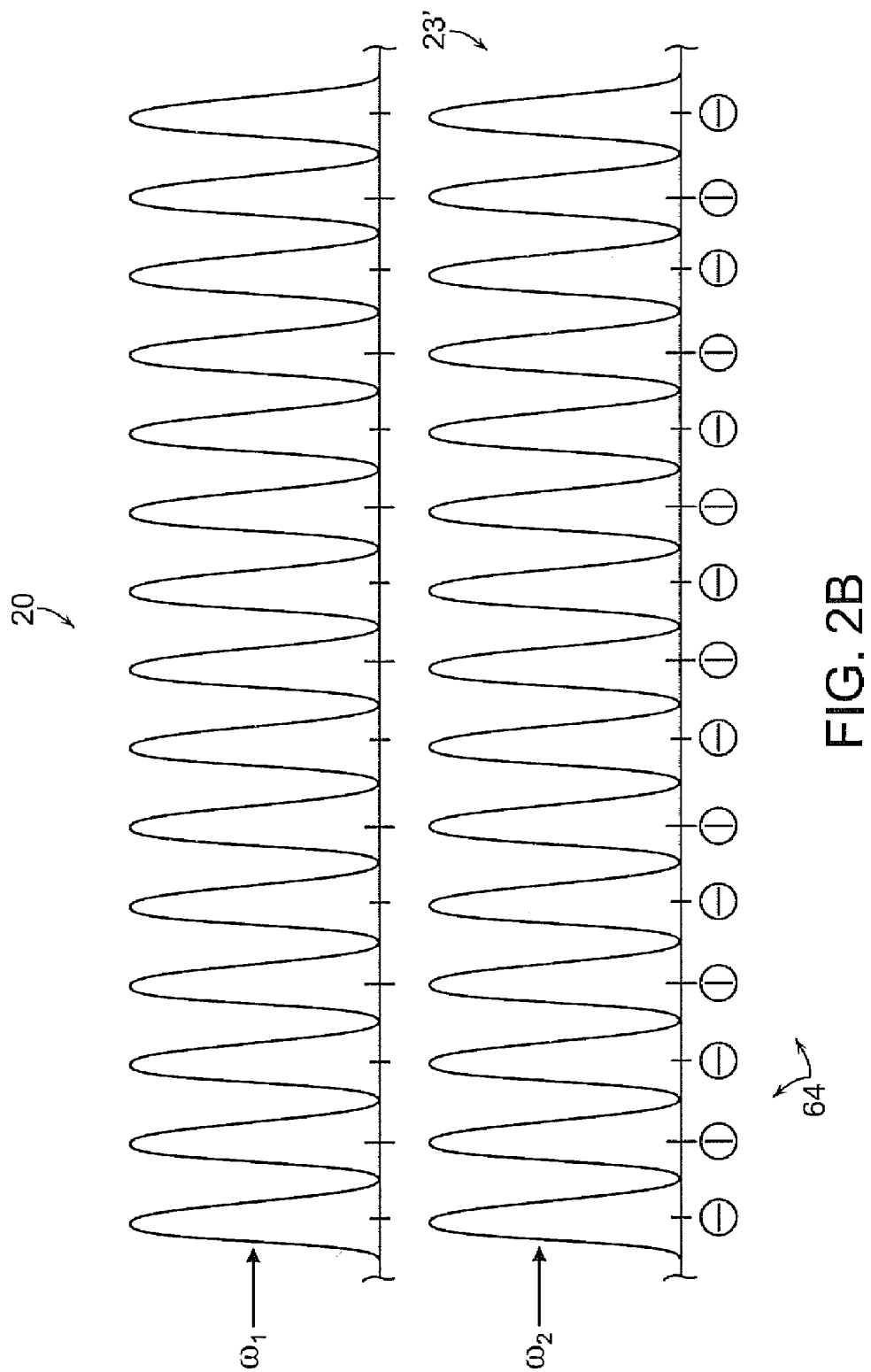

Although the use of amplitude modulation has the highest modulation depth, this approach may introduce a linear background due to a modulation of the temperature or refractive index of the sample due to the intensity modulation on the sample. In accordance with another embodiment, the modulation system may provide polarization modulation as shown at 64 in FIG. 2B, and may include a polarization device as the modulator 38, and a polarization controller as the controller 40. As shown in FIG. 2B, every other pulse of the $\omega_2$ pulse train has a polarization that is different than that of the other preceding pulse. Each of the $\omega_2$ pulses of the pulse train 23' is coincident with a $\omega_1$ pulse of the $\omega_1$ pulse train 20. Different modulation rates other than half of the repetition rate of the laser (in which every other pulse is different) can also be applied if synchronization of the modulation and the pulse train is insured electronically.

Polarization modulation also provides that stimulated Raman scattering does not substantially occur in the focal volume with the pulses having the altered unparallel polarization. In certain embodiments, the modulator includes a polarization filter to remove one of the sets of pulses as a further contrast mechanism. The polarization of the pulses may therefore, be modulated with respect to each other. In other embodiments, the detector itself may distinguish between the modulated pulses. In particular, when pump and Stokes pulse trains are perpendicular to each other, a different tensor element of the nonlinear susceptibility is probed compared to the case where pump and Stokes field are parallel. Different tensor elements have significantly different magnitudes. This converts the polarization modulation of the excitation beams into amplitude modulations of the gain/loss signal which can then be detected with the lock-in amplifier. Polarization modulation can be implemented with a Pockel cell. This approach has the advantage that it does not introduce a temperature modulation of the sample.

Figure 2C:
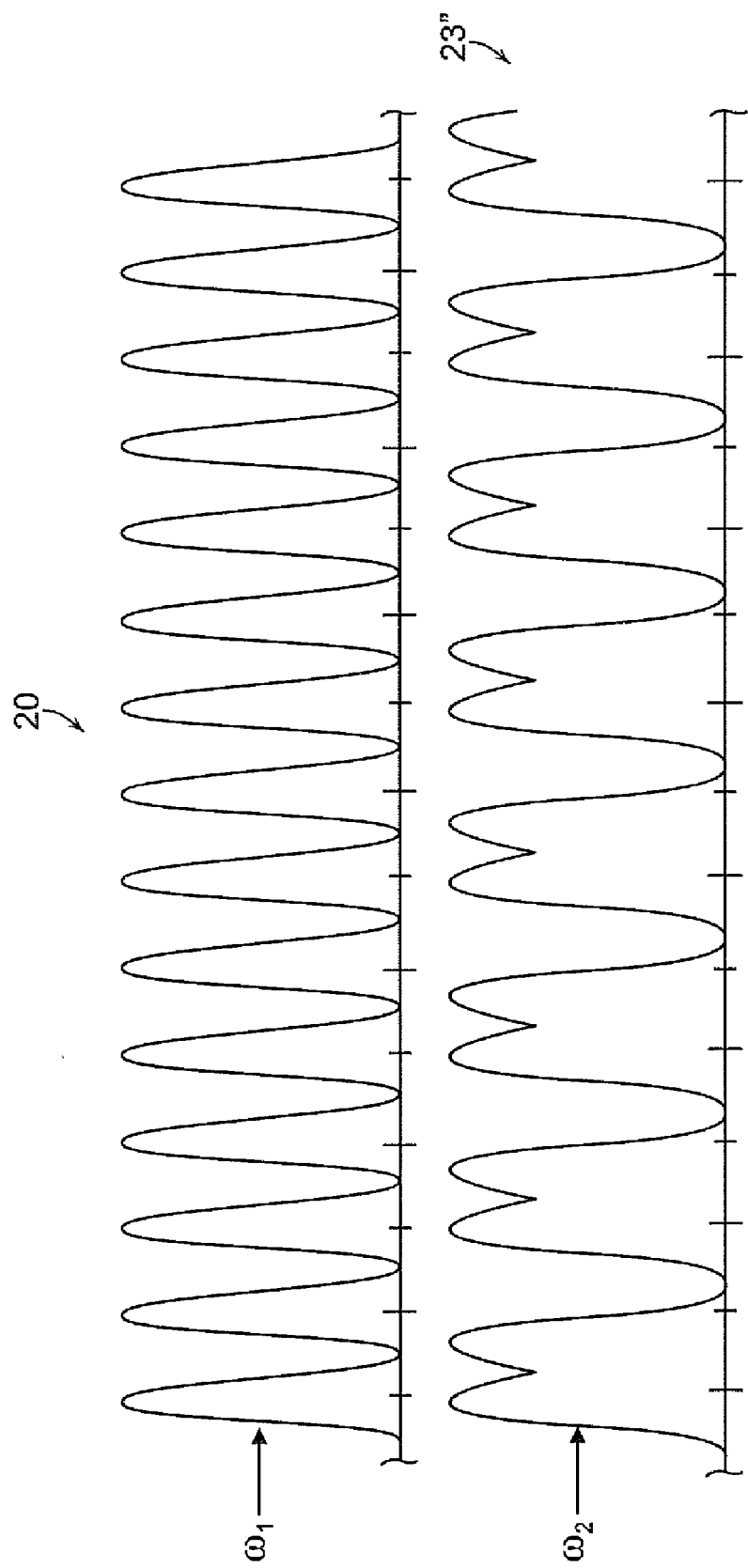

In accordance with other embodiments, one of the pulse trains may be modulated by time-shifting (or phase). FIG. 2C shows the $\omega_1$ pulse train 20 as well as a modulated $\omega_2$ pulse train 23" that includes alternating pulses that coincide with a $\omega_1$ pulse, while the remaining pulses are time shifted (as shown at 66) such that they do not coincide with a $\omega_1$ pulse.

Modulation of one or both of the pump and Stokes beams may also be achieved by frequency modulation as disclosed, for example, in U.S. Pat. No. 7,352,458, the disclosure of which is hereby incorporated by reference in its entirety. In a frequency modulation system, the frequency of one or both of the pump and Stokes beams is alternately modulated at a modulation frequency such that a difference frequency between the pump and Stokes beams (e.g., $\omega_p - \omega_S$) is tuned in and out of a vibrational frequency of the sample. The detector then detects the gain/loss that is generated through non-linear interaction of $\omega_p$ and $\omega_S$ and the sample responsive to the modulation frequency. An output signal may be passed through a lock-in amplifier such that only changes at the time scale of the modulation period are provided in the final output. In accordance with further embodiments, other modulation schemes may be employed such as time-delay modulation, spatial beam mode modulation, etc., which will each introduce a modulation of a generated signal.

Figure 2D:
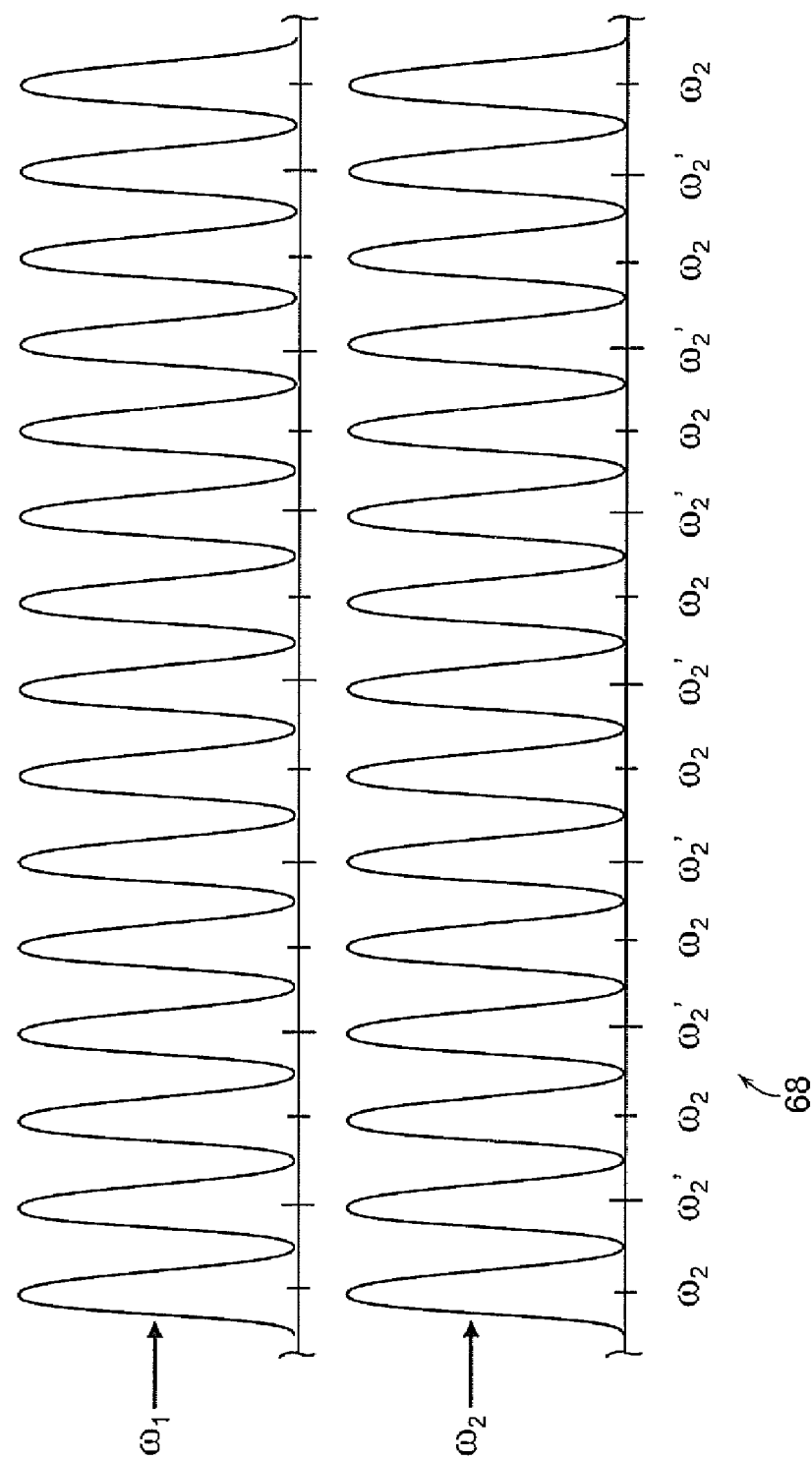
Figure 3:
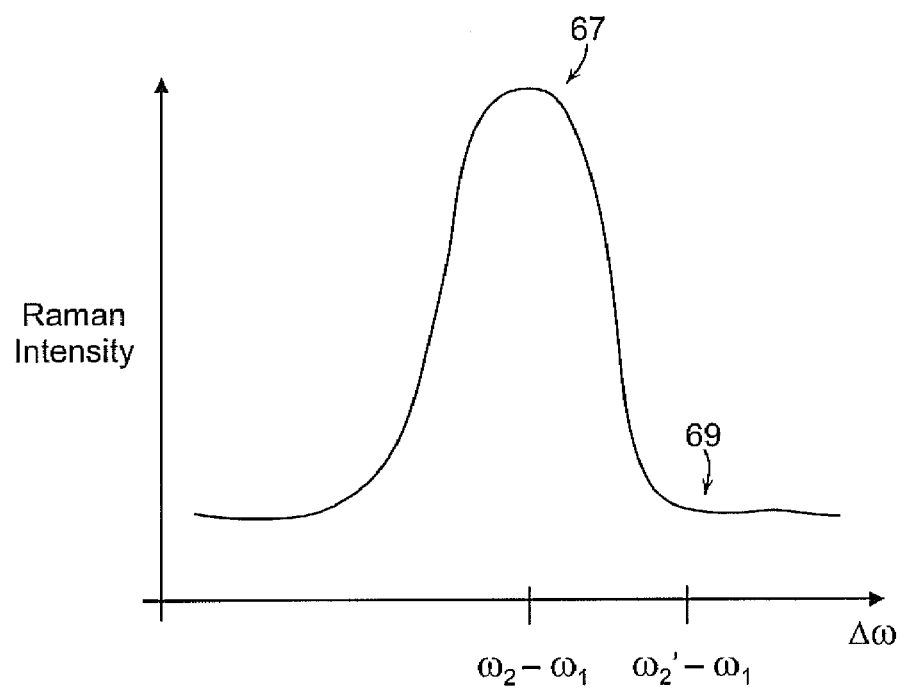
FIG. 3 shows an illustrative graphical representation of Raman intensity as a function of a difference between frequencies of two pulse trains in a system in accordance with an embodiment of the invention.

As shown in FIG. 2D, in such a frequency modulation system, the $\omega_2$ pulse train is modulated such that the pulses alternate between frequencies of $\omega_2$ and $f_2'$ as shown at 68. As shown in FIG. 3, while the difference frequency of $\omega_2 - \omega_1$ yields high Raman intensity at resonance with a sample as shown at 67, the modified difference frequency of $\omega_2' - \omega_1$ yields only a background signal as shown at 69.

Figure 4A:
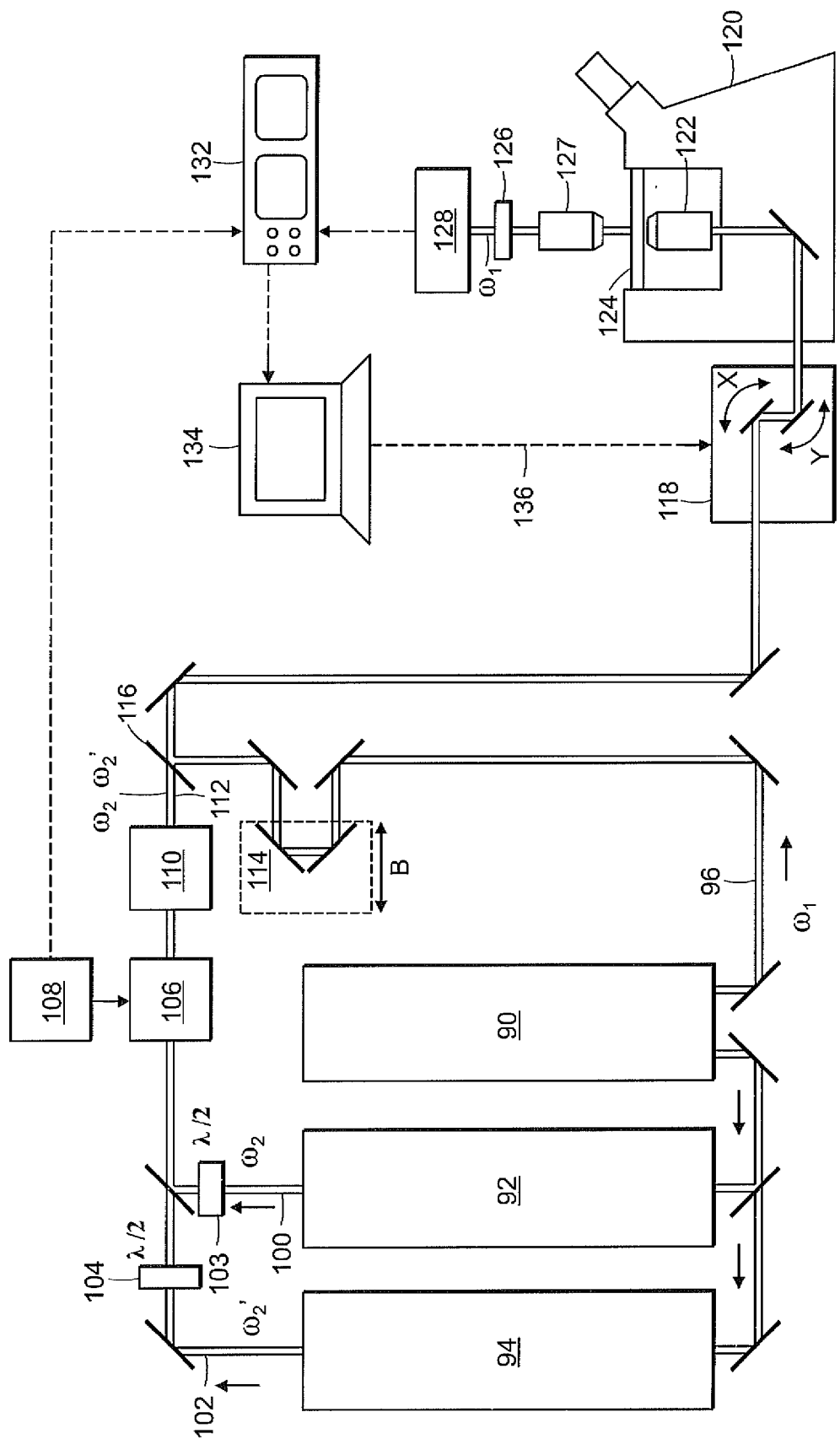
FIGS. 4A and 4B show illustrative diagrammatic views of microscopy imaging systems in accordance with further embodiments of the invention that provide frequency modulation of a train of pulses.

Systems for providing frequency modulation of a pulse train may, for example, include an additional optical parametric oscillator again, such as disclosed in U.S. Patent Application Publication No. 2008/0037595, the disclosure of which is hereby incorporated by reference in its entirety. For example, FIG. 4A shows a system that includes a dual frequency laser source 90, a first optical parametric oscillator 92, as well as an additional optical parametric oscillator 94 by splitting the power of the laser source 90. The dual frequency laser source 90 provides a train of laser pulses 96 at a center pump frequency, and a train of laser pulses 98 at a center frequency to the optical parametric oscillator 92 and to the optical parametric oscillator 94. The output of the optical parametric oscillator 92 provides a train of laser pulses 100 at a center Stokes frequency $\omega_2$ that is selected such that a difference between $\omega_1$ and $\omega_2'$ (e.g., $\omega_p - \omega_S$) is resonant with a vibrational frequency of a sample (not shown) in a focal volume. The output of the optical parametric oscillator 94 provides a train of laser pulses 102 at a center frequency $\omega_2'$ that is selected such that a difference between $\omega_1$ and $\omega_2'$ (e.g., $\omega_p - \omega_S'$) is not resonant with a vibrational frequency of the sample in the focal volume.

The $\omega_2'$ pulses are passed through a half wave plate 104 and combined with the $\omega_2$ pulses, which are passed through a different half wave plate 103. The half wave plates insure that the pulse trains have different polarization such that one is transmitted by the beam splitter and the other is reflected. At this point, the combined pulse train includes both the $\omega_2$ and the $\omega_2'$ pulses, however with orthorgonal polarization. The combined $\omega_2$ and the $\omega_2'$ pulses are passed through a modulator that, responsive to a modulation signal that provides a modulation frequency from a modulation source 108. Based on the different polarization the modulator together with a polarization analyzer selects a different polarization at the modulation rate f, i.e., it selects $\omega_2$ or $\omega_2'$ pulses. The result is that a pulse train of alternating $\omega_2$ and $\omega_2'$ pulses is provided as shown at 112. The train of laser pulses 96 may be adjusted at a translation stage 114 (that is adjustable as indicated at B) to ensure that the train of laser pulses 96 and the train of laser pulses 112 are temporally overlapped. The two trains of laser pulses 96 and 112 are combined at a combiner 116 such that they are collinear and spatially overlapped as well.

The combined trains of laser pulses 96 and 112 are directed via a scanhead 118 into a microscope 120 that includes optics 122 that direct and focus the combined trains of laser pulses 96 and 112 on a sample 124 in the focal volume as discussed above with reference to the system shown in FIG. 1. A resulting illumination is directed by a condenser 127 onto an optical detector 128, and is filtered by a filter 126 to yield only the $\omega_1$ pulse train, which is detected by the optical detector 128, such as a photodiode.

The integrated intensity of substantially all frequency components of the first pulse train 130 from the optical detector 128 is provided to the signal processor 132, and the modulation (amplitude and/or phase) of the integrated intensity of substantially all the optical frequency components of the train of laser pulses 96 due to the non-linear interaction of the train of laser pulses 112 with the train of laser pulses 96 in the focal volume is detected at the modulation frequency f to provide a pixel of an image to a microscopy control computer 134. The microscopy control computer 134 is employed as an imaging system, and further provides user control of the scanhead 118 as shown at 136.

Figure 4B:
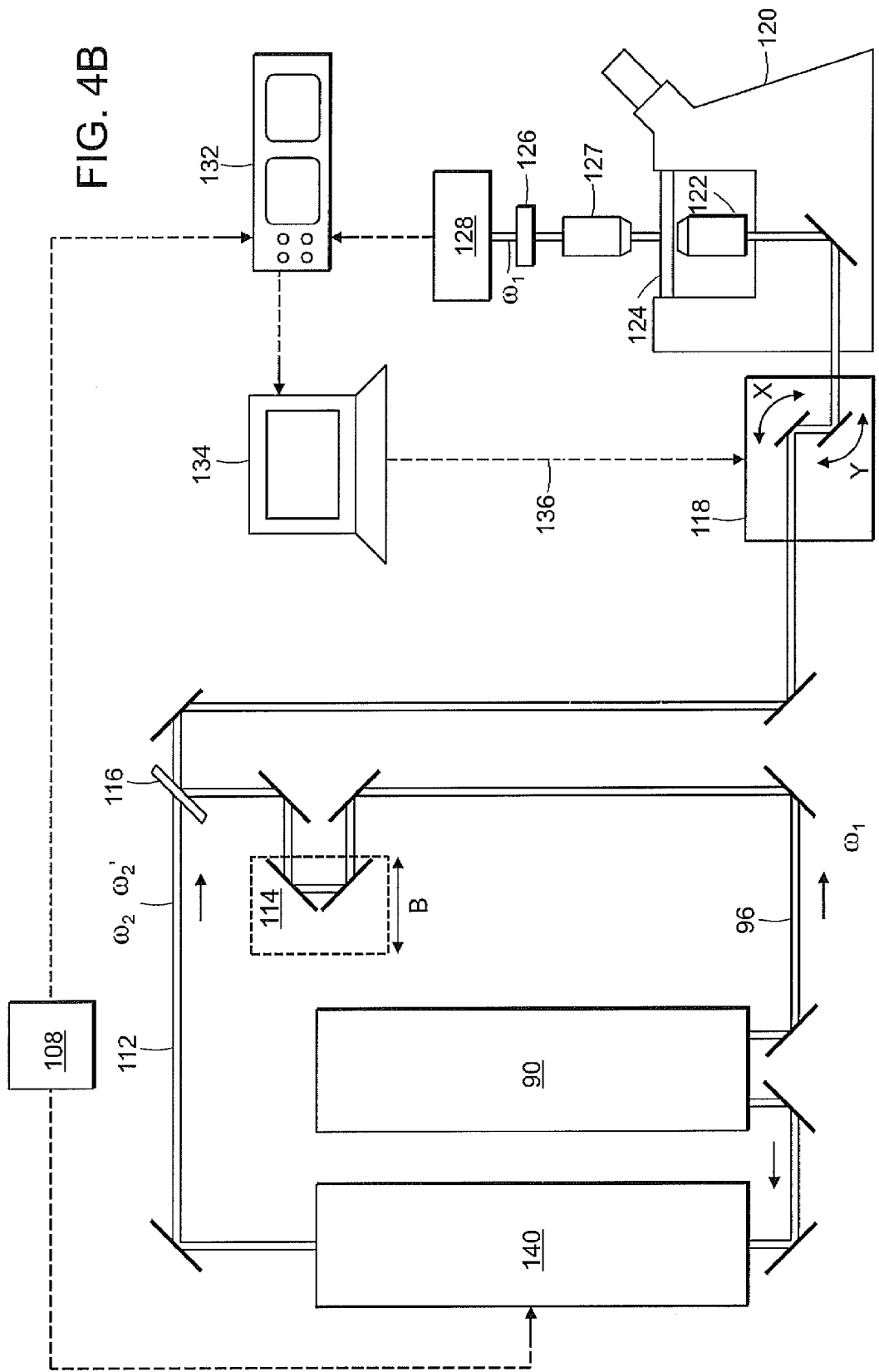

In accordance with further embodiments, the system may include an electronically locked laser such as an electronically locked titanium sapphire laser in place of the optical parametric oscillator 94. In still further embodiments, the system may include a single optical parametric oscillator for providing both the $\omega_2$ and the $\omega_2'$ pulses. For example, FIG. 4B shows a system that includes an optical parametric oscillator 140 that provides both the $\omega_2$ pulse train as well as the $\omega_2'$ pulse train. Again, a pulse train of alternating $\omega_2$ and $\omega_2'$ pulses is provided as shown at 112 with response to the modulation rate set by 108. The train of laser pulses 96 may be adjusted at a translation stage 114 (that is adjustable as indicated at B) to ensure that the train of laser pulses 96 and the train of laser pulses 112 are temporally overlapped. The two trains of laser pulses 96 and 112 are combined at a combiner 116 such that they are collinear and spatially overlapped as well.

The combined trains of laser pulses 96 and 112 in FIG. 4B are directed via a scanhead 118 into a microscope 120 that includes optics 122 that direct and focus the combined trains of laser pulses 96 and 112 on a sample 124 in the focal volume as discussed above with reference to the system shown in FIG. 1. A resulting illumination is directed by a condenser 127 onto an optical detector 128, and is filtered by a filter 126 to yield only the $\omega_1$ pulse train, which is detected by the optical detector 128, such as a photodiode. The $\omega_1$ image signal 130 from the optical detector 128 is provided to a signal processor 132, and an integrated intensity of the optical frequency components of the train of laser pulses $\omega_1$ due to the non-linear interaction of the train of laser pulses 96 with the train of laser pulses 112 in the focal volume is detected at the modulation frequency f to provide a pixel of an image to a microscopy control computer 134. The microscopy control computer 134 is employed as an imaging system, and further provides user control of the scanhead 118 as shown at 136.

If a single modulation is not sufficient to suppress the laser noise completely, two independent modulations may be combined. Two detection schemes are possible: Double-modulation and inter-modulation. With double-modulation, a first modulation is done at a higher frequency than the second and is demodulated by the first lock-in detector with a time constant that will allow passing the modulation at the second rate. The demodulated signal from the first lock-in amplifier will therefore still possess the second modulation that is demodulated with a second lock-in amplifier. With inter-modulation, two independent modulations have similar rates and the signal is detected at the sum or difference frequency of the modulation rates with a single lock-in amplifier. A system such as a Stanford Research SR844FM lock-in amplifier, CanOptics 360-80 Pockel cell may be used to achieve this.

The realization of Raman gain/loss microscopy relies on the right combination of the excitation laser source, signal detection based phase-sensitive detection and laser scanning microscopy. Again with reference to FIG. 1, the signal is generated if two pulse trains of frequency $\omega_p$ (pump beam) and $\omega_S$ (Stokes beam) interact in the sample and $\Delta\omega=\omega_S-\omega_p$ equals the frequency of a molecular vibration of the molecule in focus. Due to the interaction the pump beam is depleted and the Stokes beam is increased. Which molecular species is detected is chosen prior to the imaging by tuning $\Delta\omega$ into the Raman resonance of the molecule of interest. Thus Raman Gain/Loss measurements require two overlapped lasers beams, ideally with tunable wavelength to address different $\Delta\omega$. Pulsed lasers with higher peak field strengths increase the size of the signal and thus lower the pixel dwell time. The signal is a small decrease (Raman Loss)/increase (Raman Gain) of the intensity of the pump/Stokes beam and as such sits on the background of the intensities of the excitation beams. It can be separated from this background by amplitude modulation and phase-sensitive detection. This allows the determination of the concentration of the vibrationally resonant molecule species in the focal spot. By scanning the focal spot through the sample, i.e., in a beam scanning microscope, a 3-dimensional image of the distribution of the selected molecular specimen can acquired.

The choice of laser pulse width is critical in this nonlinear microscopy. The signal 10 depends nonlinearly on the excitation intensities as it is proportional to the product $I_{Pump} \cdot I_{Stokes}$, where $I_{Pump}$ and $I_{Stokes}$ are the intensities of the pump and Stokes beam respectively. As such the signal can be increased by using pulsed lasers with high peak intensities of $I_{Pump}$ and $I_{Stokes}$ but the same average intensity on the sample. However, the pulse-width of the laser-pulse $\Delta t$ and its bandwidth in frequencies $\Delta\omega$ are related by the equation $\Delta t \cdot \Delta\omega = \text{const}$. So in order to produce a short pulse one requires a spectrally broad pulse. The typical line-width of a Raman band is ~30 cm$^{-1}$ which corresponds to a pulse-width of ~2-3 ps if the laser bandwidth is chosen to match the line-width of the Raman band. Utilizing a longer pulse-width will sacrifice the peak intensities and therefore decrease the non-linear signal. Utilizing a shorter pulse-width with a greater number of contributing frequencies will not increase the signal further as most of the excitation is off vibrational resonance. This unnecessarily increases the power on the sample and thus the photo-damage. Thus the use of laser with a typical pulse-width of several ps is ideal. For this pulse-width a repetition rate of ~80 MHz is ideal to decrease photodamage of the sample. In order to focus into the same spot which is necessary to generate the signal (spatial overlap) the beams have to be parallel and of same divergence. When pulsed lasers are used the pulses have to occur at the same time (temporal overlap), i.e. the repetition rate of the two beams has to be equal and the time delay has to be adjustable to overlap the pulsed or intrinsically zero.

At least one of the pump or Stokes pulses should have tunable wavelength to allow the choice or scanning of a Raman band, i.e., a molecular species. The wavelength should be adjustable to at least ~0.1 nm precision as Raman bands have a typical width of 0.5 nm.

The use of lasers in the near IR (700 nm-1500 nm) has advantages for biomedical imaging as penetration depth is maximized and photodamage is minimized due to minimal absorption and scattering at these wavelengths. Thus there is no limitation to use the technique in vivo or on human patients. In some occasions of the use of visible and UV lasers can be useful to boost the signal (through electronic enhancement), sacrificing the advantages of penetration depth and photodamage with near IR sources. A possible solution is the combination of a synchronously pumped OPO and a pump-laser. Saturable absorbers can tune the pulsewidth (SEASAM technology). Typical gain media generate light at 1064 nm which can then be frequency doubled to 532 nm to pump an OPO generating a signal beam at 700 nm-1000 nm and an idler beam at 1100 nm-2000 nm. Either signal and/or idler beam can be used (signal+idler) or they can be combined with some of the 1064 nm light that has not been frequency doubled respectively (signal+1064 nm or idler+1064 nm). Due to the synchronous pumping, the repetition rate is matched automatically. Signal and idler beam are overlapped in time intrinsically and the timedelay between the signal/idler and the 1064 nm output can be achieved with a delay stage. Alternatively synchronized Ti:Sa laser or fiber-lasers can be used. A commercially available system such as a HighQ Picotrain+APE Berlin Emeral OPO may be used.

The signal is detected with a photodiode. In the shot-noise limit (relative signal noise ~1/√(number of photons detected)) the imaging speed can be increased by increasing the number of photons detected maintaining the same relative noise. Thus it is important that the photodiode allows to detect high laser intensities (typically ~200 mW). The use of a large-area photodiode allows small variation of the detected signal even if the beams are slightly moving on the photodiode (see non-descanned detection below). However the response-time has to be short enough to allow high-frequency modulation. Silicon or Gennanium diodes allow covering the necessary wavelength regime in the near IR. A commercially available system such as a Thorlabs FDS1010 system may be used.

A high optical density blocking filter is needed in front of the light detector to suppress the modulated pump beam (for Raman Gain microscopy) or Stokes beam (for Raman Loss microscopy) respectively, while pass the wanted Stokes beam or pump beam. A system such as a Chroma Tech 890/220 band-bass filter (for Raman Loss microcopy) may be used to block 1046 Stokes beam while pass the pump beam.

The challenge on the detection side is to extract the signal from a huge background as the technique measures a small intensity increase (Raman Gain)/decrease (Raman Loss) off the strong laser intensities:

$$\text{Intensity after the sample} \approx |E_0 \pm \Delta E|^2 = E_0^2 \pm \Delta E \cdot E_0 + \Delta E^2$$

Where $E_0$ is the electric field of the excitation beam (Stokes beam for Raman Gain and pump beam for Raman Loss) and $\Delta E$ is the radiation at the same frequency due to the nonlinear third-order induced polarization. Because of the coherent increase/decrease the resulting laser intensity after the sample (proportional to the absolute value of the electric field squared) consists of the original laser intensity, the coherent mixing term and the quadratic term of the field change. For typical samples and laser intensities used, the mixing term is more than 5 orders of magnitude lower and the quadratic term is more than 10 orders of magnitude lower than the intensity of the incoming laser beam. Thus the quadratic term is negligible and the challenge of the detection is to extract the relatively small heterodyning term from the huge laser background. If this suppression is incomplete, laser-noise scaling with the background overwhelms the relatively small signal.

High-frequency modulation with phase-sensitive detection is employed to extract the heterodyning signal from the background. Some type of modulation is used to modulate the intensity of the signal (amplitude modulation) keeping the background constants. In a frequency perspective the signal occurs at the modulation frequency $\omega_{mod}$ whilst the background is DC. By electronically filtering out all contributions but the signal at $\omega_{mod}$ it is possible to reject the background. The bandwidth of this filter is $\sim 1/T_{int}$, where $T_{int}$ is the integration time constant (equals the pixel dwell time). Considering phase with respect to the modulation as a second characteristic of the signal compared to the background and its noise, a more complete suppression is possible. A lock-in amplifier may be used to achieve this.

Figure 5:
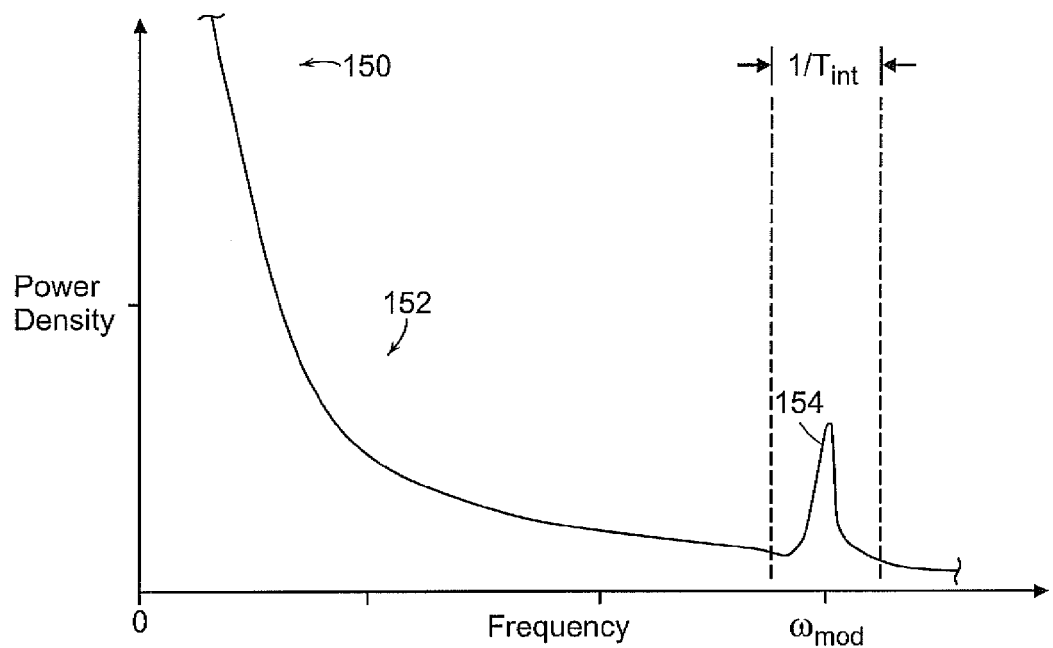
FIG. 5 shows an illustrative graphical representation of the power spectrum of the laser, its noise and the signal modulation in the frequency-domain in accordance with an embodiment of the invention.

FIG. 5, for example, shows diagrammatically the power spectrum of the laser, including DC power at 150, the intensity of 1/f noise at 152, and a signal at 154 that is filtered using a filter having a width of about $1/T_{int}$ that is centered at the modulation frequency.

The excitation lasers are not constant in intensity but have intensity noise which is spectrally broad. This introduces components of the laser (not the signal) at $\omega_{mod}$ which are purely due to noise and would limit the sensitivity of the technique if not minimized. The intensity of the laser noise typically depends inversely on the frequency (1/f noise). Thus by choosing $\omega_{mod}$ high enough the contribution from the laser-noise within the detection-bandwidth of the lock-in amplifier becomes small. For the OPO system described above a modulation >1 MHz will typically suppress the laser-noise completely, or makes the laser noise negligible compared to the signal size.

For maximum sensitivity and lowest background it is important that the transmitted beam does not pass any aperture between the sample and the photodiode that 'clips' the edges of the beam. Because of the 'cross phase modulation' the modulation (intensity or polarization) of the pump/Stokes beam modulates the refractive index of the sample in focal spot. In other words the pump/Stokes beam generates an instantaneous 'microslens' in the focus, which results in a slightly different beam-divergence of the transmitted Stokes/pump-beam that is detected with the photodiode. If the Stokes/pump-beam undergoes any spatial filtering, for example by an aperture, this beam-profile-modulation results in an intensity modulation exactly at the modulation frequency that is detected with the lock-in amplifier. Thus, substantially any kind of media would introduce a non-resonant background. If the resonant signal from the species to be detected is much smaller than this background, it can be buried in the laser-noise associated with this unwanted background.

Spatial filtering of the transmitted beam can be avoided to a large extent. For example, a high numerical aperture (NA) condenser may be used, as this determines which angles of incident light on the condenser are collected. Especially the NA of the condenser has to be equal or higher than the NA of the objective. The highest possible NA should be used for the light collection excitation objective. The optical path may also be designed to avoid apertures smaller than the beam diameter. To avoid beam-clipping it is however necessary that the beam is smaller than the active area of the photodiode to avoid aperture effects.

A microscopy technique is provided by providing a Raman gain or loss signal to an imaging system to determine the concentration of a molecular species in the focal volume. By scanning the focal spot through the sample and measuring the signal for every pixel it is possible to build up a 3-dimensional image of the distribution of the molecular species. This scanning may be done either by beam-scanning (scan the focal spot through the fixed sample by changing the angles of the beams at the back-aperture of the objective with respect to normal incident), stage-scanning (moving the sample with respect to the fixed focal spot) or any combination. With beam-scanning, scan-rates as high as 7000 lines/s can be achieved, it is mechanically more stable and does not perturb the sample as is remains unmoved. Most commercially available confocal microscopes use a combination of beam-scanning in the xy-plane and stage-scanning in z. An Olypus FV-300 or FV-1000 system, Leica SP5, or Zeiss LSM 510 or LSM 710 system may be used for this.

Figure 9:
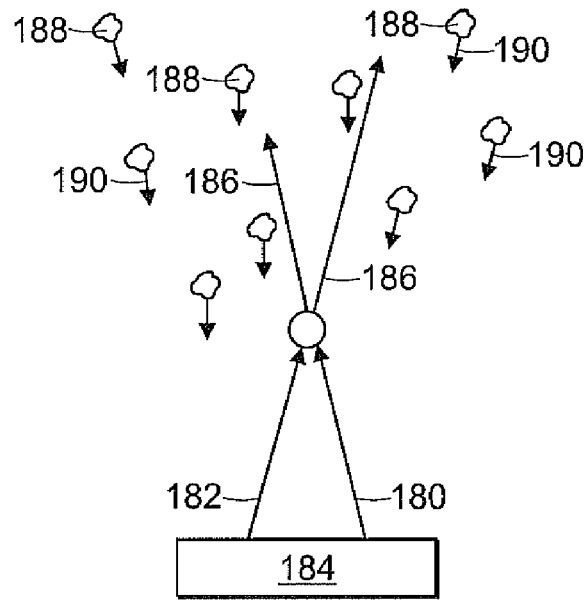
FIG. 9 shows an illustrative diagrammatic view of the non-linear interaction of a first train of pulses with the second train of pulses in a common focal volume in accordance with an embodiment of the invention; and in particular shows how the forward traveling light may be backscattered by the sample and detected in the epi-direction employing epi-directed detection.

Because Raman Gain/Loss results in an increase/depletion of the excitation beams it is better be detected in the forward for transparent samples. In highly scattering samples as tissue, the forward traveling light is however back-scattered as illustrated in FIG. 9. Thus detection is possible and necessary in epi-direction for scattering samples. As such, Raman Gain/Loss microscopy has the potential to be implemented for endoscopic imaging.

As the generated intensity depends non-linearly on the excitation intensities the signal is only generated in the focal spot. As such Raman Gain/Loss microscopy is intrinsically 3-dimensional section which makes a pin-hole unnecessary. This allow to use non-descanned detectors as close to the sample as possible to collect maximum signal. In the forward direction it is possible to use two lenses in a '4-f-geometry' to image the back aperture of the objective onto the photodiode, i.e. image the scan-mirror onto the photodiode. In minimize the motion of the beam on the photodiode as the non-descanned detection is used.

Raman Loss microscopy was implemented in a modified Olympus FV-300 microscope using the tunable signal beam (pump beam) from the APE Berlin Emerald OPO and the 1064 nm output (Stokes beam) from the HighQ pump laser. The signal was detected in forward direction with a Thorlabs FDS 1010 large area photodiode and the 1064 nm beam was blocked with a Chroma 890/220 band-pass filter after passing through the focus and the sample. Polarization modulation of the Stokes beam with the ConOptics 360-80 Pockel Cell at 1 MHz was used to introduce the amplitude modulation of the signal which was then extracted with a Stranford Research SR844RF lock-in amplifier. Proper RF-shielding was critical to get rid of RF-pickoff from the high-voltage driving of the Pockel cell.

Figure 7:
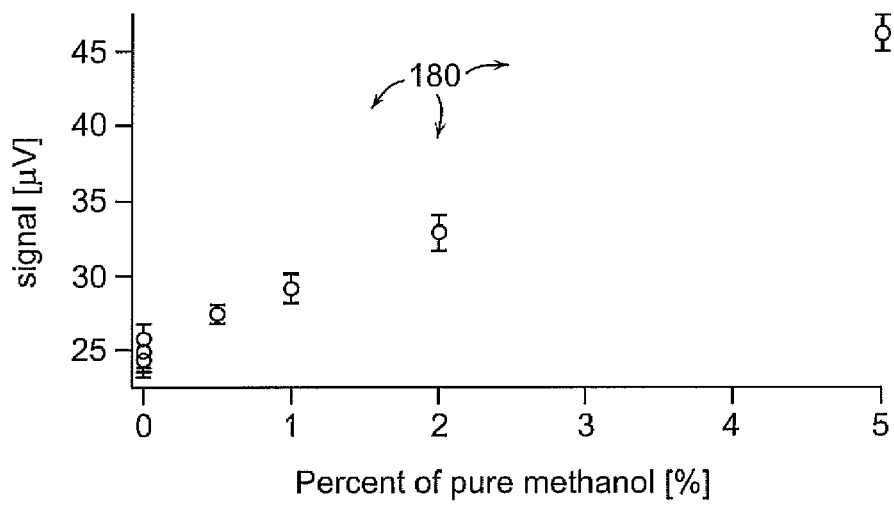
FIG. 7 shows an illustrative graphical representation of the concentration of methanol/water solution that can be detected in a system in accordance with an embodiment of the invention.

The Raman Loss spectrum of pure methanol was recorded by scanning the wavelength of the pump beam and keeping the power on the sample constant. The same double-peak structure as with spontaneous Raman was recovered and no non-resonant background is detected as expected. As shown at 180 in FIG. 7, the current detection limit was found to be 0.5% methanol in water which is already lower than the one for normal CARS microscopy. Implementation of double-modulation or inter-modulation and switching to longer wavelengths will further increase the sensitivity. A linear concentration dependence of the loss signal on the methanol concentration was found as expected.

Figure 6:
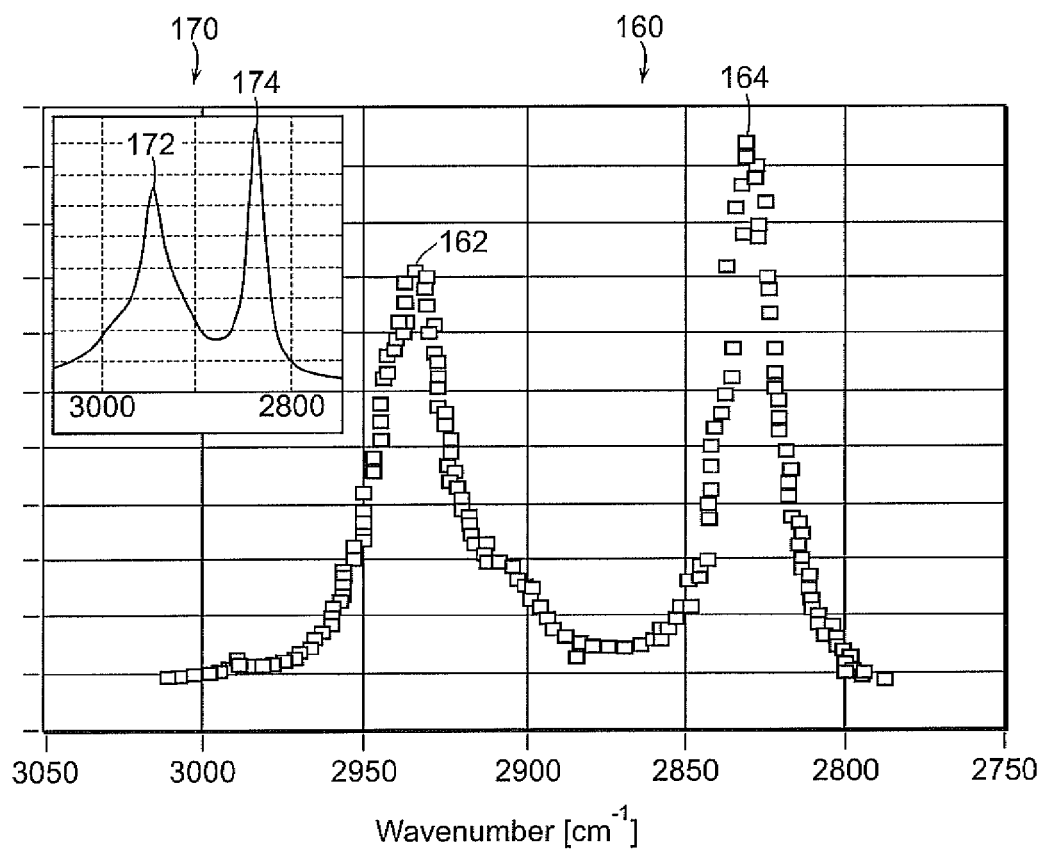
FIG. 6 shows an illustrative graphical representation of a Raman loss spectrum of methanol using a system in accordance with an embodiment of the invention that employs scanning the pump wavelength at constant power, and further shows the spontaneous Raman spectrum of methanol as measured by a conventional confocal Raman spectroscopic system.

FIG. 6 shows a Raman loss spectrum 160 for methanol that was acquired in a system in accordance with an embodiment of the invention that includes two characteristic peaks 162 and 164. FIG. 6 also shows at the insert thereof, that these results well match the conventional known Raman loss spectrum for methanol as shown at 170 having characteristic peaks 172 and 174.

Figure 8:
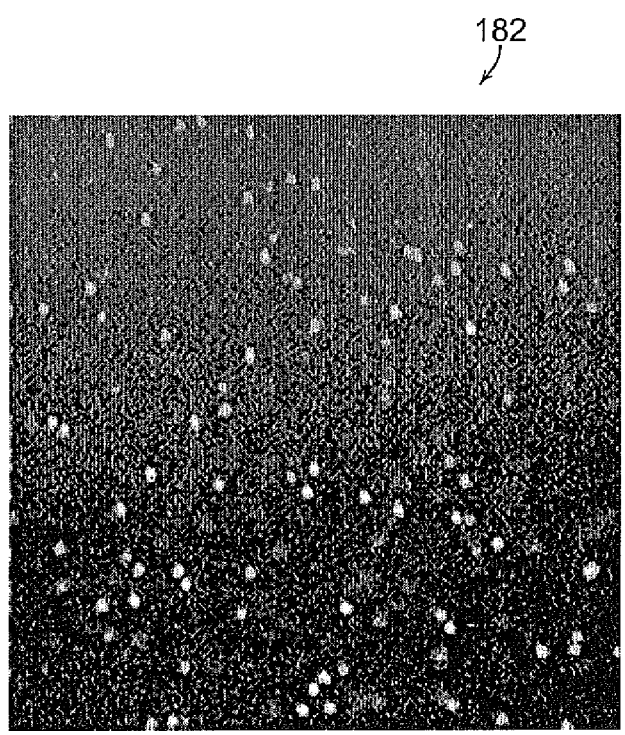
FIG. 8 shows an illustrative microscopy output image of polystyrene beads having a diameter of 1 μm and dispersed in 2% agarose gel solution as detected by a system in accordance with an embodiment of the invention.

One half percent (0.5%) imaging was demonstrated for 1 μm polystyrene beads in 2% agarose gel in water as shown at 182 in FIG. 8. No non-resonant background as for CARS was found. Imaging was performed with a pixel-dwell-time of 100 μs. Shorter or longer pixel-dwell-times are possible.

As shown in FIG. 9, during the non-linear interaction of the modulated Stokes train of pulses (shown diagrammatically at 180) and the pump train of laser pulses (shown diagrammatically at 182) when focused through optics 184, both the pump and Stokes pulses are directed in a forward direction (as show diagrammatically at 186). A detector that is positioned forward of the sample will detect forward directed Stokes pulses that pass through the sample.

As also shown in FIG. 9, during the non-linear interaction of the modulated Stokes train of pulses (180) and the pump train of laser pulses (182) when focused through optics 184, some pump and Stokes pulses are reflected by elements 188 within the sample (as show diagrammatically at 190) back toward the optics 184. In accordance with other embodiments therefore, a detector may also be positioned in the reverse direction with respect to the incoming pump and Stokes pulse trains that are directed into the focal volume. In such as reverse direction detection system, the detector will detect reflected pump pulses.

Figure 10:
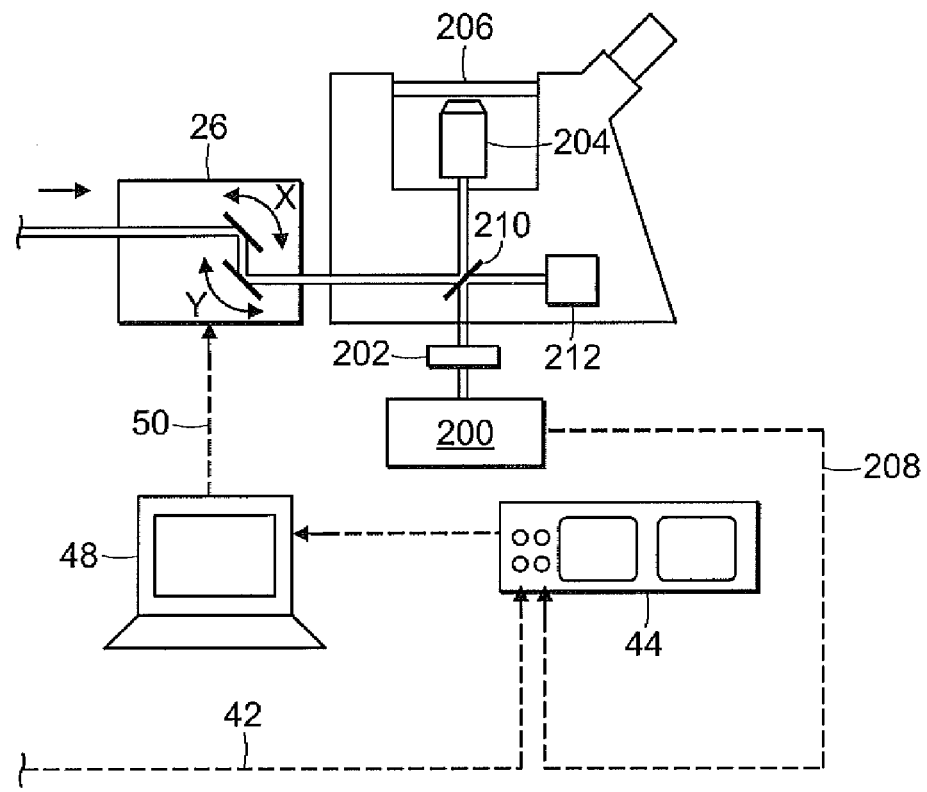
FIG. 10 shows an illustrative diagrammatic view of a portion of a microscopy imaging system in accordance with another embodiment of the invention employing epi-directed detection.

FIG. 10 shows a portion of system in accordance with a further embodiment of the invention in which system components having the same reference numerals as used in FIG. 1 are the same as those in FIG. 1. The remaining elements from FIG. 1 not shown in FIG. 10 are the same, and the system may provide amplitude modulation, polarization modulation, phase modulation or frequency modulation as discussed above.

The system of FIG. 10, however, employs an optical detector 200 that receives via a filter 202 an integrated intensity of the optical frequency components of the train of Stokes pulses that are reflected through the common focal volume. In particular, the optics 204 directs and focuses the two trains of laser pulses onto a sample 206 in the focal volume, and illumination that is directed in the epi-direction (by reflecting off other material in the sample following Raman scattering) is directed back through the optics 204 onto the optical detector 200 via filter 202. The image signal 208 is provided to the signal processing unit 44, which is in communication with the microscopy control computer 48 as discussed above with reference to FIG. 1.

As signal and excitation beam have the same optical frequency, the system may provide that the beam splitter 210 is a 50/50 splitter that reflects 50% of an incident beam and transmits 50% of the incident beam through the beam splitter onto a heat absorber 212. This would ideally provide that 25% of the Stokes beam would be transmitted back into the detector 200. In further embodiments, the beam splitter 210 may be a 20/80 splitter that reflects 20% of an incident beam and transmits 80% of the incident beam through the beam splitter, resulting in 4% signal on the detector 200. As with the embodiments discussed above, the system may provide modulation at a modulation frequency f, such as amplitude modulation, polarization modulation, phase modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 11:
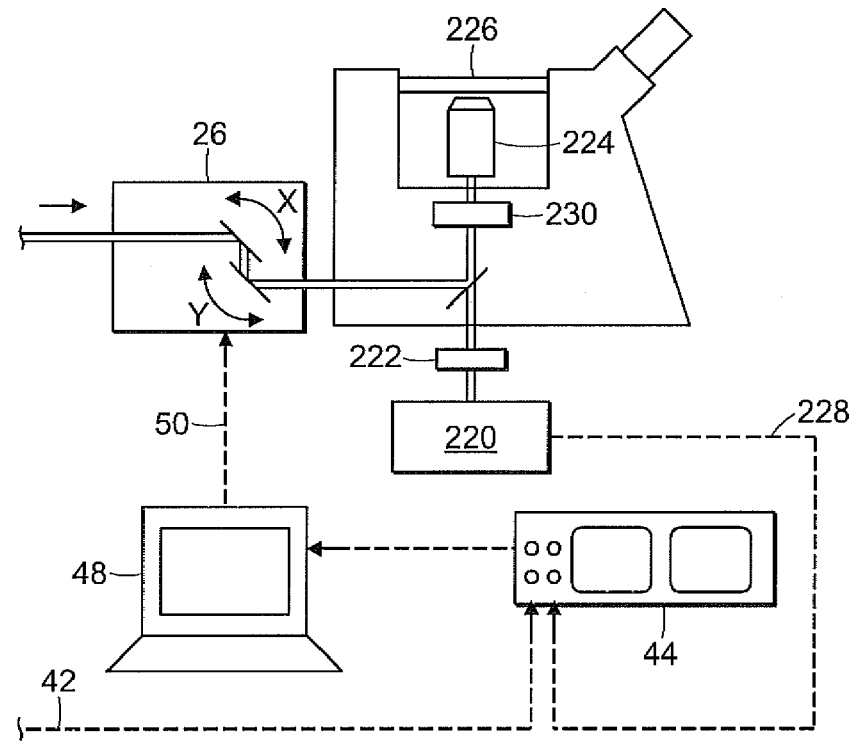
FIG. 11 shows an illustrative diagrammatic view of a portion of a microscopy imaging system in accordance with a further embodiment of the invention employing epi-directed detection.

FIG. 11 shows a portion of system in accordance with a further embodiment of the invention in which system components having the same reference numerals as used in FIG. 1 are the same as those in FIG. 1. The remaining elements from FIG. 1 not shown in FIG. 11 are the same, and the system may provide amplitude modulation, polarization modulation, phase modulation or frequency modulation as discussed above.

The system of FIG. 11 employs an optical detector 220 that receives via a filter 222 an integrated intensity of the optical frequency components of the train of pump or Stokes pulses that are reflected through the common focal volume. In particular, the optics 224 directs and focuses the two trains of laser pulses onto a sample 226 in the focal volume, and illumination that is directed in the epi-direction (by reflecting off of other material in the sample following Raman scattering) is directed back through the optics 224 onto the optical detector 220 via filter 222. The image signal 228 is provided to the signal processing unit 44, which is in communication with the microscopy control computer 48 as discussed above with reference to FIG. 1.

In the system of FIG. 1 signal and excitation beams of the same optical frequency are separated by employing quarter wave plate 230 prior to the optics 224, as well as a polarization beam splitter. This arrangement provides that substantially all of the incident Stokes pulse train from the OPO 14 (polarized in a first orientation by the OPO) is reflected, but that when pump and Stokes pulses are directed from the focal volume back through the device 230, the Stokes pulses are at 90 degrees polarization with respect to the original Stokes pulses, and are transmitted through the polarization beam splitter toward the detector 220 via the filter 222. As with the embodiments discussed above, the system may provide modulation at a modulation frequency f, such as amplitude modulation, polarization modulation, phase modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 12:
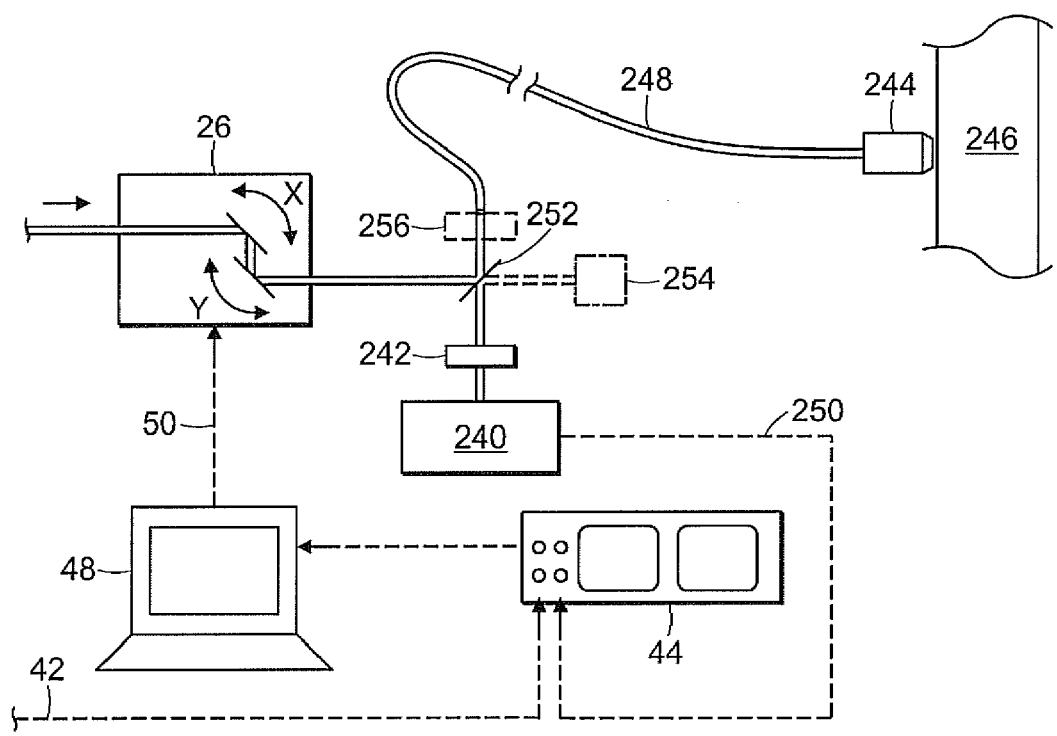
FIG. 12 shows and illustrative diagrammatic view of a microscopy imaging system in accordance with a further embodiment of the invention employing an optical fiber delivery and detection system.

FIG. 12 shows a portion of system in accordance with a further embodiment of the invention in which system components having the same reference numerals as used in FIG. 1 are the same as those in FIG. 1. The remaining elements from FIG. 1 not shown in FIG. 12 are the same, and the system may provide amplitude modulation, polarization modulation, phase modulation or frequency modulation as discussed above.

The system of FIG. 12 employs an optical detector 220 that receives via a filter 242 an integrated intensity of the optical frequency components of the train of Stokes pulses that are reflected through the common focal volume. In particular, the optics 244 directs and focuses the two trains of laser pulses onto a sample 246 in the focal volume via an optical fiber system 248, and illumination that is directed in the epi-direction (by reflecting off of other material in the sample following Raman scattering) is directed back through the optics 244 and optical fiber system 248 onto the optical detector 240 via filter 242. The image signal 250 is provided to the signal processing unit 44, which is in communication with the microscopy control computer 48 as discussed above with reference to FIG. 1.

In the system of FIG. 12, reflection of the Stokes pulses from the focal volume back into the optical parametric oscillator (OPO) 14 (shown in FIG. 1) may be inhibited by using a 50/50 or 20/80 beam splitter 252 and heat sink 254 as discussed above with reference to FIG. 10, or may be inhibited by employing quarter wave plate 256 and having the beam splitter be instead a polarization beam splitter as discussed above with reference to FIG. 11. As with the embodiments discussed above, the system may provide modulation at a modulation frequency f, such as amplitude modulation, polarization modulation, phase modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 13:
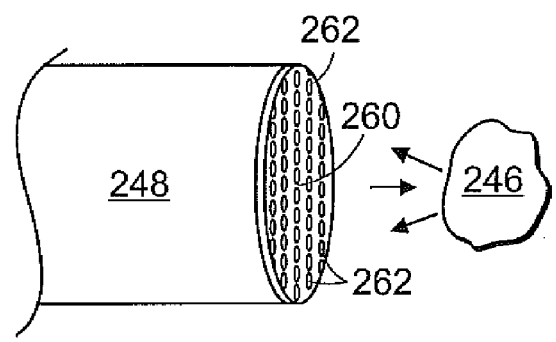
FIG. 13 shows a diagrammatic illustrative view of a distal portion of an optical fiber system that may be used as the optical fiber in the system of FIG. 12 in accordance with an embodiment of the invention.

As shown in FIG. 13, the optical fiber system 248 (of FIG. 12) may include multiple individual fibers, and the pump and Stokes pulse trains from the laser sources (12, 14) may be provided in one optical fiber 260, while reflected pump and Stokes pulses from the sample 246 are directed back through the optical fiber system 248 via different optical fibers 262. The system may include a 50/50 or 20/80 beam splitter 252 and heat sink 254 as discussed above with reference to FIG. 10, or may be inhibited by employing quarter wave plate 256 and having the beam splitter be instead a polarization beam splitter as discussed above with reference to FIG. 11. As with the embodiments discussed above, the system may provide modulation at a modulation frequency f, such as amplitude modulation, polarization modulation, time-delay modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 14:
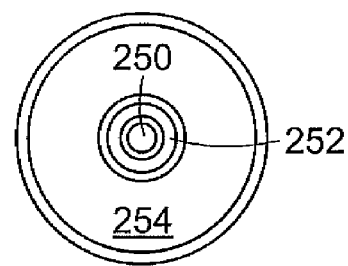
FIG. 14 shows a diagrammatic illustrative cross-sectional view of another optical fiber system that may be used as the optical fiber in the system of FIG. 12 in accordance with another embodiment of the invention.

In other embodiments, the optical fiber system 248 (of FIG. 12) may include separate pump, Stokes, and collection fibers as shown in FIG. 14. In such a system, the pump pulse train may be provided through a fiber 250, while a modulated Stokes pulse train is provided through a fiber 252, and collection fibers 254 may be employed to direct reflected pump illumination back through the optical fiber system 248. The system may also include a 50/50 or 20/80 beam splitter 252 and heat sink 254 as discussed above with reference to FIG. 10, or may be inhibited by employing quarter wave plate 256 and having the beam splitter be instead a polarization beam splitter as discussed above with reference to FIG. 11. As with the embodiments discussed above, the system may provide modulation at a modulation frequency f, such as amplitude modulation, polarization modulation, phase modulation or frequency modulation, and the processor detects a modulation (amplitude and/or phase) of the integrated intensity of substantially all of the optical frequency components of the Stokes pulse train due to the non-linear interaction of the Stokes pulse train with the pump pulse train within the common focal volume.

Figure 15:
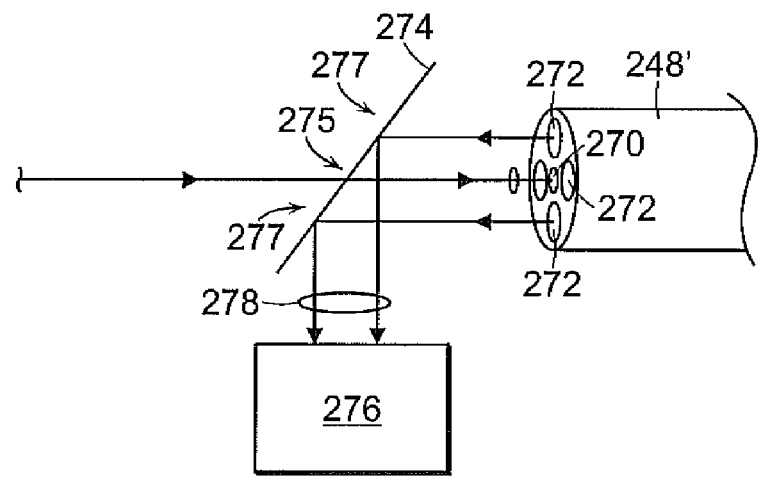
FIG. 15 shows an illustrative diagrammatic view of a proximal portion of another optical fiber system that may be used in a system as shown in FIG. 12 in accordance with a further embodiment of the invention.

As shown in FIG. 15, in accordance with further embodiments, an optical fiber system 248' (such as shown in FIG. 12) may include multiple individual fibers, and the pump and Stokes pulse trains from the laser sources (12, 14) may be provided in one optical fiber 270, while reflected pump and Stokes pulses from the sample are directed back through the optical fiber system via different optical fibers 272. The system of FIG. 15 may include a beam splitter 274 through which the pump and Stokes pulse trains from the laser sources are directed toward the proximal end of the optical fiber system. In particular, the beam splitter 274 may either include a small central transmissive region 275 where the collinear pump and Stokes trains of pulses contact the beam splitter, and a highly reflection region 277 surrounding the central transmissive region 275. Reflected pump and Stokes pulses from the sample that are directed back through the optical fiber system via the optical fibers 272 are directed by the beam splitter 274 toward an optical detector 276 via a lens 278. As with the embodiments discussed above, the system may provide modulation at a modulation frequency f, such as amplitude modulation, polarization modulation, phase modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

Figure 16:
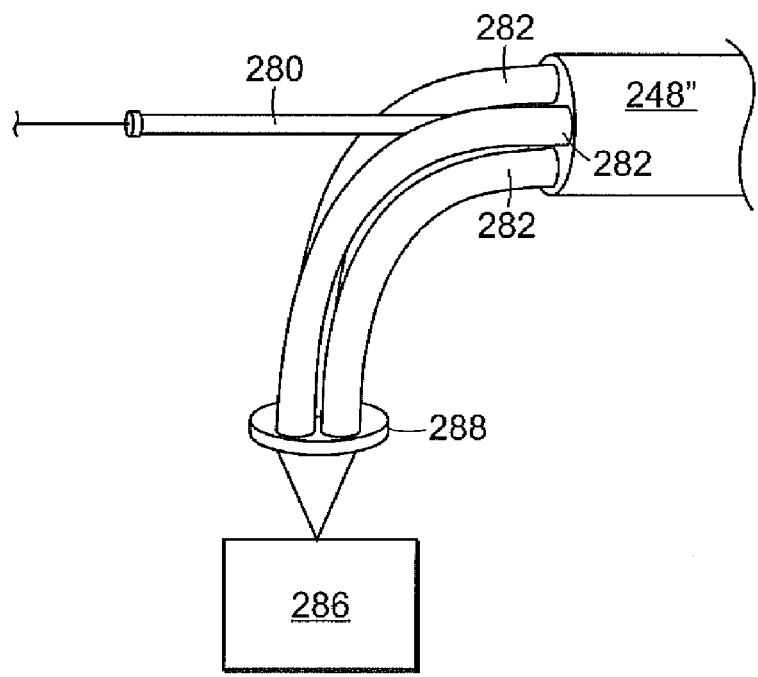
FIG. 16 shows an illustrative diagrammatic view of a proximal portion of a further optical fiber system that may be used in a system as shown in FIG. 12 in accordance with a further embodiment of the invention.

As shown in FIG. 16, in accordance with further embodiments, an optical fiber system 248" (such as shown in FIG. 12) may include multiple individual fibers, and the pump and Stokes pulse trains from the laser sources (12, 14) may be provided in one optical fiber 280, while reflected pump and Stokes pulses from the sample are directed back through the optical fiber system via different optical fibers 282. The system of FIG. 16 may separate the optical fibers 282 from the optical fiber 280 at the proximal end such that the reflected pump and Stokes pulses from the sample that are directed back through the optical fiber system via the optical fibers 282 are directed toward an optical detector 286 via a lens 288. As with the embodiments discussed above, the system may provide modulation at a modulation frequency f such as amplitude modulation, polarization modulation, phase modulation or frequency modulation, and the processor 44 detects a modulation (amplitude and/or phase) of the integrated intensity of substantially all of the optical frequency components of the Stokes pulse train due to the non-linear interaction of the Stokes pulse train with the pump pulse train within the common focal volume.

In further embodiments, the system may include a proximal and/or distal scanning systems for controllably adjusting the position of the trains of pump and/or Stokes pulses with respect to the optical fibers as disclosed, for example in U.S. Pat. No. 7,414,729, the disclosure of which is hereby incorporated by reference in its entirety. Either or both of the pump and Stokes trains of pulses for example, may be directed toward different fibers, and in further embodiments, the system may also include a distal scanning system for controllably adjusting the position of the collinear trains of pump and Stokes pulses with respect to the sample such that the collinear trains of pump and Stokes pulses may be directed toward any of the multiple regions in x, y and z directions within the sample as disclosed.

Figure 17:
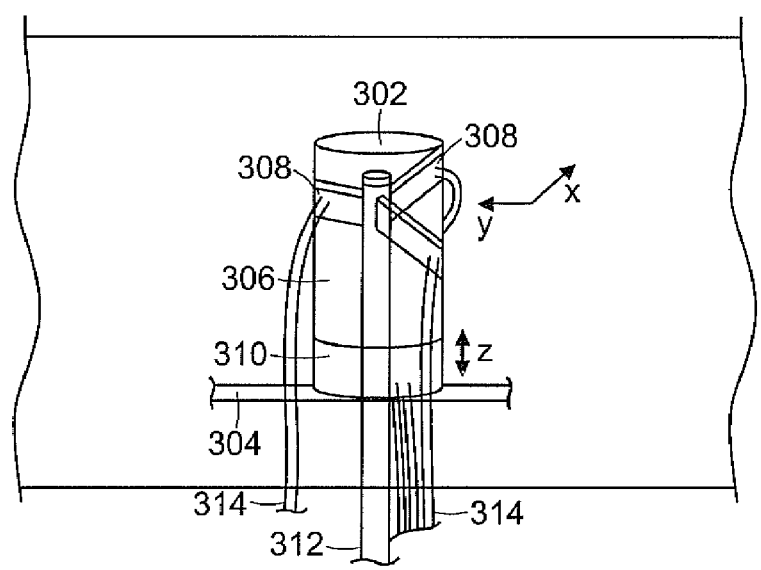
FIG. 17 shows a distal scanning system that may be employed with a system as shown in FIG. 12 in accordance with a further embodiment of the invention.

As shown in FIG. 17, for example, in accordance with further embodiments, the focal position of the pump and Stokes fields may be scanned within a sample by a scanning system that is provided at the distal end of the optical fiber. The distal scanning system of FIG. 17 includes a housing 302 that includes fixed and moving portions 304 and 306 respectively, as well as x and y direction piezoelectric motors 308, and a z axis annular-shaped piezoelectric motor 310. The optical fiber system 312 may then be delivered into the housing 302 and electrical control lines 314 may be brought back to outside of the patient.

Figure 18A:
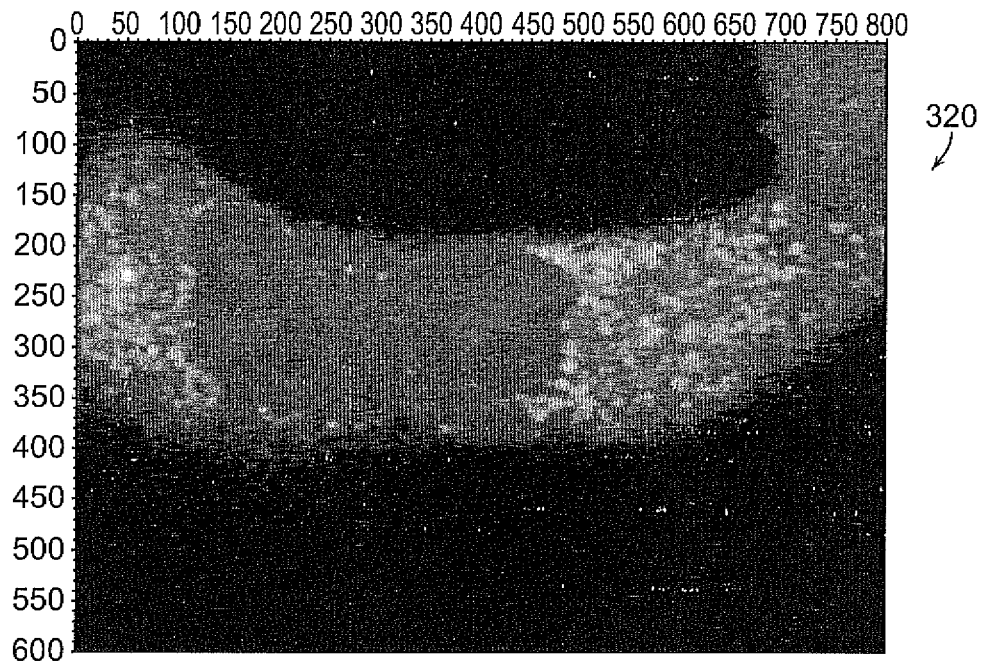
FIGS. 18A and 18B show on-resonance and off-resonance illustrative microscopy images of mammalian cancer cells using a microscopy system in accordance with an embodiment of the invention.
Figure 18B:
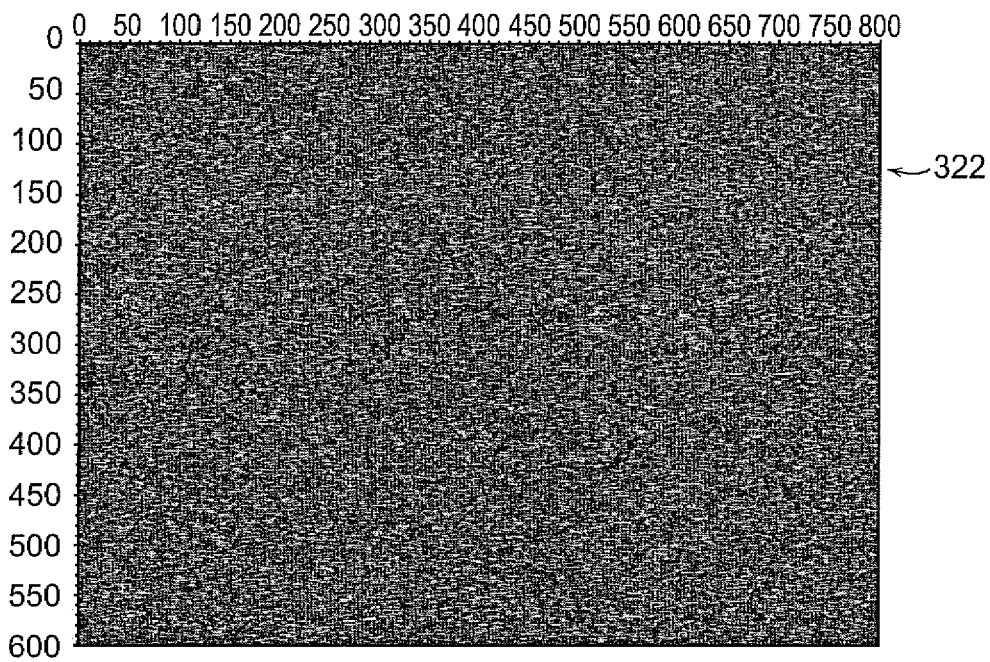

FIGS. 18A and 18B show on-resonance and off-resonance illustrative microscopy images of mammalian cancer cells using a microscopy system in accordance with an embodiment of the invention. The image shown at 320 in FIG. 18A was taken when a system of the invention was tuned into the $CH_2$ stretching vibration of mammalian cancer cells, and the lipid distribution in the cell may be clearly seen. The image shown at 322 in FIG. 18B was taken off resonance, and the chemical contrast completely vanishes. Note that in a modulated CARS microscopy system, a resonant image would still occur when off resonance, which reduces the contrast capabilities of the modulation.

Those skilled in the art will appreciate that numerous modifications and variations may be made to the above disclosed embodiments without departing from the spirit and scope of the claims.

What is claimed is:

1. A microscopy imaging system comprising:
a first light source for providing a first train of pulses at a first center optical frequency $\omega_1$;
a second light source for providing a second train of pulses at a second center optical frequency $\omega_2$ such that a difference between $\omega_1$ and $\omega_2$ is resonant with a vibrational frequency of a sample in the focal volume, wherein the second train of pulses is synchronized with the first train of pulses;
a modulator system for modulating a property of the second train of pulses at a modulation frequency f of at least 100 kHz;
focusing optics for directing and focusing the first train of pulses and the second train of pulses toward a common focal volume;
an optical detector for detecting an integrated intensity of substantially all optical frequency components of the first train of pulses transmitted or reflected through the common focal volume by blocking the second train of pulses; and
a processor for detecting a modulation at the modulation frequency f, of the integrated intensity of substantially all of the optical frequency components of the first train of pulses due to the non-linear interaction of the first train of pulses with the second train of pulses in the common focal volume, to provide a pixel of an image for the microscopy imaging system.

2. The microscopy system as claimed in claim 1, wherein said microscopy system employs stimulated Raman spectroscopy as a contrast mechanism, and wherein the first train of pulses provides a pump beam, and the second train of pulses that is modulated by the modulator system at the modulation frequency f provides a Stokes beam such that a Raman loss is detected at the signal processor at the modulation frequency f.

3. The microscopy system as claimed in claim 1, wherein said microscopy system employs stimulated Raman spectroscopy as a contrast mechanism, and wherein the first train of pulses provide a Stokes beam, and the second train of pulses that is modulated by the modulator system at the modulation frequency f provides a pump beam such that a Raman gain is detected at the signal processor at the modulation frequency f.

4. The microscopy system as claimed in claim 1, wherein said modulator provides amplitude modulation of the second train of laser pulses.

5. The microscopy system as claimed in claim 1, wherein said modulator provides polarization modulation of the second train of laser pulses.

6. The microscopy system as claimed in claim 1, wherein said modulator provides time-shift (phase) modulation of the second train of laser pulses.

7. The microscopy system as claimed in claim 1, wherein said modulator provides frequency modulation of the second train of laser pulses.

8. The microscopy system as claimed in claim 1, wherein said modulator provides double-modulation or inter-modulation of the second train of laser pulses.

9. The microscopy system as claimed in claim 1, wherein said optical detector is positioned in a forward direction with respect to the first and second trains of pulses entering the common focal volume.

10. The microscopy system as claimed in claim 1, wherein said optical detector is positioned in a reverse direction with respect to the first and second trains of pulses entering the common focal volume.

11. The microscopy system as claimed in claim 1, wherein said system further includes collecting optics for directing illumination from the focal volume toward the optical detector, and wherein the collecting optics has a numerical aperture that is at least as high as a numerical aperture of the focusing optics.

12. The microscopy system as claimed in claim 1, wherein said system further includes collecting optics for directing illumination from the focal volume toward the optical detector, and wherein the collecting optics is non-imaging optics.

13. The microscopy system as claimed in claim 1, wherein said first and second trains of pulses are directed toward the common focal volume via an optical fiber or fiber bundle.

14. The microscopy system as claimed in claim 1, wherein said first train of pulses is detected from the common focal volume via an optical fiber or fiber bundle.

15. The microscopy system as claimed in claim 1, wherein said first and second trains of pulses are directed toward the common focal volume via a first optical fiber system, and wherein said first train of pulses is detected from the common focal volume via a second optical fiber system.

16. The microscopy system as claimed in claim 1, wherein said modulation frequency f is at least 1 MHz.

17. The microscopy system as claimed in claim 1, wherein said modulator system includes any of an electro-optical modulator or an acousto-optical modulator.

18. The microscopy system as claimed in claim 1, wherein said microscopy system includes a scanning mechanism that permits one of the common focal volume and the sample to be moved in three dimensions with respect to one another such that multiple pixels of the image for the microscopy imaging system may be obtained.

19. The microscopy system as claimed in claim 1, wherein at least one of the first and second light sources includes a synchronously pumped optical parametric oscillator.

20. The microscopy system as claimed in claim 1, wherein at least one of the first and second light sources includes an electronically locked mode locked laser.

21. The microscopy system as claimed in claim 1, wherein at least one of the first and second light sources includes a broad band source from which at least two narrow bands within the broad band source band are employed.

22. The microscopy system as claimed in claim 1, wherein at least one of the first and second light sources is generated from an optical fiber that is either narrowband having a pulse width in the picosecond range, or is broadband having a pulse width in the femtosecond range.

23. The microscopy system as claimed in claim 1, wherein the modulator includes a modulated optical parametric oscillator or modulated mode-locked laser.

24. The microscopy system as claimed in claim 1, wherein the modulator includes an electronically locked mode locked laser.

25. The microscopy system as claimed in claim 1, wherein the signal processor includes an electronic passive frequency filter.

26. The microscopy system as claimed in claim 1, wherein the signal processor includes a lock-in amplifier.

27. The microscopy system as claimed in claim 1, wherein the signal processor includes a box car detector for time domain analysis.

28. The microscopy system as claimed in claim 1, wherein both the first and the second trains of pulses have a pulse width of between about 0.2 picoseconds to about 10 picoseconds.

29. A method of providing microscopy imaging, said method comprising the steps of:
    providing a first train of pulses at a first center optical frequency $\omega_1$;
    providing a second train of pulses at a second center optical frequency $\omega_2$ such that a difference between $\omega_1$ and $\omega_2$ is resonant with a vibrational frequency of a sample in the focal volume, wherein the second train of pulses is synchronized with the first train of pulses;
    modulating of a beam property of the second train of pulses at a modulation frequency f of at least 100 kHz;
    directing and focusing the first train of pulses and the second train of pulses toward a common focal volume;
    detecting an integrated intensity of substantially all optical frequency components of the first train of pulses transmitted or reflected through the common focal volume by blocking the second train of pulses; and
    detecting a modulation at the modulation frequency f, of the integrated intensity of the substantially all of the optical frequency components of the first train of pulses due to the non-linear interaction of the first train of pulses with the second train of pulses in the common focal volume, to provide a pixel of an image for the microscopy imaging system.

30. The method as claimed in claim 29, wherein said method employs stimulated Raman spectroscopy as a contrast mechanism, and wherein the first train of pulses provide a pump beam, and the second train of pulses that is modulated at the modulation frequency f provides a Stokes beam such that a Raman loss is detected at the modulation frequency f.

31. The method as claimed in claim 29, wherein said method employs stimulated Raman spectroscopy as a contrast mechanism, and wherein the first train of pulses provide a Stokes beam, and the second train of pulses that is modulated at the modulation frequency f provides a pump beam such that a Raman gain is detected at the modulation frequency f.

32. The method as claimed in claim 29, wherein said step of modulating the second train of pulses at a modulation frequency f of at least 100 kHz involves providing amplitude modulation of the second train of laser pulses.

33. The method as claimed in claim 29, wherein said step of modulating the second train of pulses at a modulation frequency f of at least 100 kHz involves providing polarization modulation of the second train of laser pulses.

34. The method as claimed in claim 29, wherein said step of modulating the second train of pulses at a modulation frequency f of at least 100 kHz involves providing phase modulation of the second train of laser pulses.

35. The method as claimed in claim 29, wherein said step of modulating the second train of pulses at a modulation frequency f of at least 100 kHz involves providing frequency modulation of the second train of laser pulses.

36. The method as claimed in claim 29, wherein said first and second trains of pulses are directed toward the common focal volume via a first optical fiber system, and wherein said first train of pulses is detected from the common focal volume via a second optical fiber system.

37. The system as claimed in claim 1, wherein a modulation characteristic is at least one of amplitude or phase of the integrated intensity of substantially all of the optical frequency components of the first pulse train.

38. The method as claimed in claim 29, wherein a modulation characteristic is at least one of amplitude or phase of the integrated intensity of substantially all of the optical frequency components of the first pulse train.

39. The microscopy system as claimed in claim 1, wherein said microscopy system includes a scanning mechanism that permits one of the common focal volume and the sample to be moved in at least one dimension with respect to one another such that multiple pixels of the image for the microscopy imaging system may be obtained.

40. The microscopy system as claimed in claim 39, wherein said microscopy system includes a scanning mechanism that permits one of the common focal volume and the sample to be moved in two dimensions with respect to one another such that multiple pixels of the image for the microscopy imaging system may be obtained.

41. The method as claimed in claim 29, wherein said method further includes the steps of:
    scanning one of the common focal volume and the sample in at least one dimension with respect to one another; and
    providing an image comprised of a plurality of pixels in a microscopy imaging system, wherein each pixel is associated with a scanning position.

42. The method as claimed in claim 41, wherein said step of scanning one of the common focal volume and the sample involves scanning in at least two dimensions with respect to one another.

43. The method as claimed in claim 41, wherein said step of scanning one of the common focal volume and the sample involves scanning in three dimensions with respect to one another.

* * * * *